United States Patent [19]

Kamiya et al.

[11] 4,299,829

[45] * Nov. 10, 1981

[54] 2-LOWER ALKYL-7-SUBSTITUTED-2 OR 3-CEPHEM 4-CARBOXYLIC ACID COMPOUNDS

[75] Inventors: Takashi Kamiya, Suita; Takao Takaya, Sakai, both of Japan

[73] Assignee: Fujisawa Pharmaceutical Co., Ltd., Osaka, Japan

[*] Notice: The portion of the term of this patent subsequent to May 1, 1996, has been disclaimed.

[21] Appl. No.: 915,459

[22] Filed: Jun. 14, 1978

Related U.S. Application Data

[63] Continuation-in-part of Ser. No. 836,909, Sep. 26, 1977, Pat. No. 4,152,433, and Ser. No. 862,606, Dec. 20, 1977, abandoned, which is a continuation-in-part of Ser. No. 836,909, , which is a continuation-in-part of Ser. No. 808,615, Jun. 21, 1977, abandoned.

[30] Foreign Application Priority Data

Jun. 28, 1976 [JP] Japan .................................. 51/26740
Jan. 5, 1977 [JP] Japan ..................................... 52/262
Dec. 13, 1977 [JP] Japan ................................ 52/150276

[51] Int. Cl.³ .......................................... C07D 501/20
[52] U.S. Cl. ...................................... 424/246; 544/16; 544/22; 544/21
[58] Field of Search ...................... 544/30, 16, 21, 22; 424/246

[56] References Cited

U.S. PATENT DOCUMENTS 3,883,517  5/1975  Heusler et al. ...................... 424/246
4,152,433  5/1979  Kamiya et al. ...................... 548/194

FOREIGN PATENT DOCUMENTS 2,412,513  9/1974  Fed. Rep. of Germany .
2461993  3/1975  Fed. Rep. of Germany .
2556736  6/1976  Fed. Rep. of Germany .

*Primary Examiner*—Nicholas S. Rizzo
*Attorney, Agent, or Firm*—Oblon, Fisher, Spivak, McClelland & Maier

[57] ABSTRACT

Compounds of the formula:

$$R^3 \underset{S}{\overset{N}{\diagdown}} \text{—A—CONH—} \underset{O}{\overset{}{\diagdown}} \underset{N}{\overset{S}{\diagdown}} R^1 \atop R^2$$

wherein $R^1$ is ($C_1$ to $C_6$) alkyl.
$R^2$ is carboxy or a protected carboxy group,
$R^3$ is amino or a protected amino group and
A is hydroxyimino ($C_1$ to $C_6$) alkylene or ($C_1$ to $C_6$)-alkoxyimino ($C_1$ to $C_6$) alkylene, and pharmaceutically acceptable salt thereof, have been found to be active against various pathogenic microorganisms.

14 Claims, No Drawings

2-LOWER ALKYL-7-SUBSTITUTED-2 OR 3-CEPHEM 4-CARBOXYLIC ACID COMPOUNDS

CROSS REFERENCE TO RELATED APPLICATIONS

The present application is a continuation in part application of Ser. No.: 836,909; filed: Sept. 26, 1977 now U.S. Pat. No. 4,152,433 and a continuation in part application of Ser. No.: 862,606; filed: Dec. 20, 1977 now abandoned. The said Ser. No. 862,606 is in turn, also a continuation in part of the said Ser. No. 836,909. Application Ser. No. 836,909 is in turn a continuation in part of application Ser. No. 808,615; filed: June 21, 1977 now abandoned.

The present invention relates to new 2-lower alkyl-7-substituted-2 or 3-cephem-4-carboxylic acid compounds and pharmaceutically acceptable salts thereof. More particularly, it relates to new 2-lower alkyl-7-substituted-2 or 3-cephem-4-carboxylic acid compounds and pharmaceutically acceptable salts thereof which have antimicrobial activities and to process for the preparation thereof, to pharmaceutical composition comprising the same, and to a method of using the same therapeutically in the treatment of infectious diseases in human being and animals.

Accordingly, it is one object of the present invention to provide 2-lower alkyl-7-substituted-2 or 3-cephem-4-carboxylic acid compounds and pharmaceutically acceptable salts thereof, which are active against a number of pathogenic microorganisms.

Another object of the present invention is to provide processes for the preparation of 2-lower alkyl-7-substituted-2 or 3-cephem-4-carboxylic acid compounds and pharmaceutically acceptable salts thereof.

A further object of the present invention is to provide pharmaceutical composition comprising, as active ingredients, said 2-lower alkyl-7-substituted-2 or 3-cephem-4-carboxylic acid compounds and pharmaceutically acceptable salts thereof.

Still further object of the present invention is to provide a method for the treatment of infectious diseases caused by pathogenic bacteria in human being and animals.

The object 2-lower alkyl-7-substituted-2 or 3-cephem-4-carboxylic acid compounds are novel and can be represented by the following general formula (I).

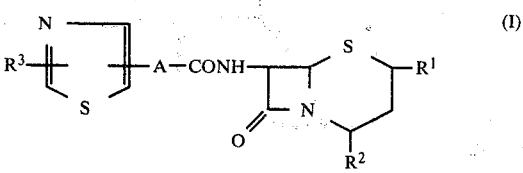

wherein
R$^1$ is lower alkyl,
R$^2$ is carboxy or a protected carboxy group,
R$^3$ is amino or a protected amino group and
A is hydroxyimino(lower)alkylene or lower alkoxyimino(lower)alkylene.

According to the present invention, the 2-lower alkyl-7-substituted-2 or 3-cephem-4-carboxylic acid compounds (I) can be prepared by various processes which are illustrated by the following schemes.

Process 1.

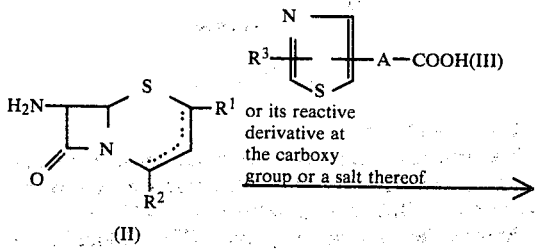

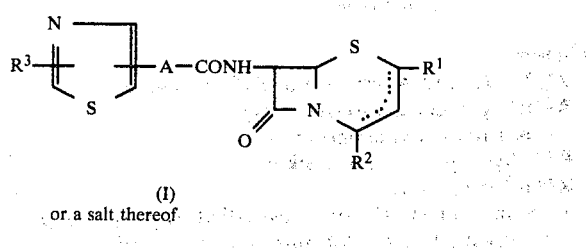

Process 2

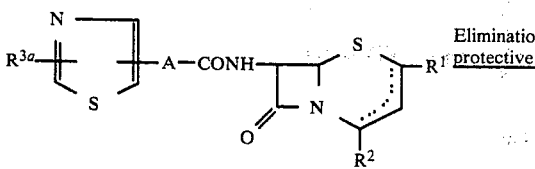

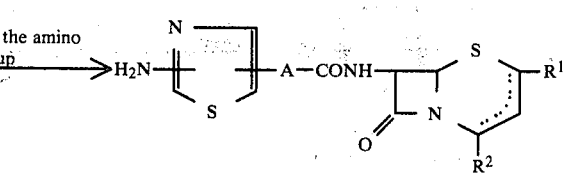

Process 3

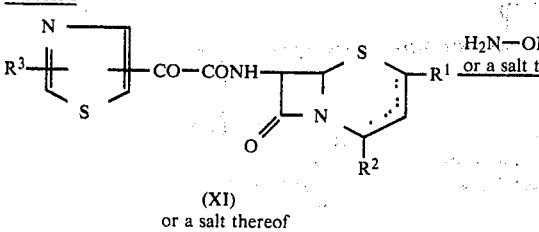

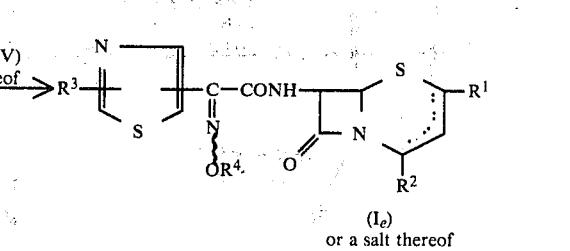

Process 4

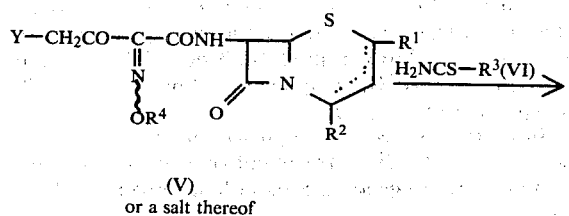 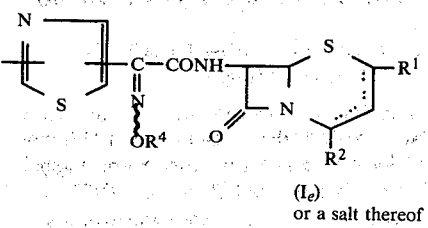

(V) or a salt thereof
(I_e) or a salt thereof

Process 5

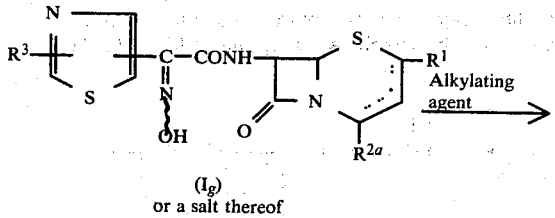

(I_g) or a salt thereof
(I_f) or a salt thereof

Process 6

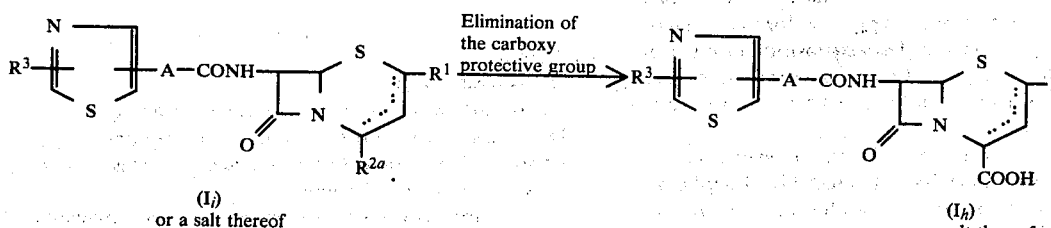

(I_i) or a salt thereof
(I_h) or a salt thereof

Process 7

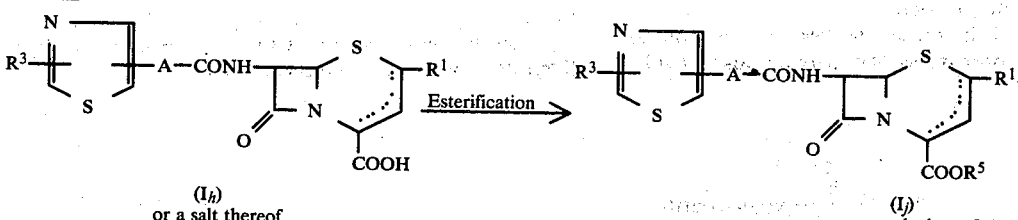

(I_h) or a salt thereof
(I_j) or a salt thereof wherein
$R^1$, $R^2$, $R^3$ and A are each as defined above,
$R^{2a}$ is a protected carboxy group,
$R^{3a}$ is a protected amino group,
$R^4$ is hydrogen or lower alkyl,
$R^{4a}$ is lower alkyl,
$R^5$ is an ester moiety of an esterified carboxy group represented by the formula: $-COOR^5$ and Y is a residue of an acid.

The starting compound (II) in the present invention can be prepared according to the methods described in W. German Offenlegungsschrift No. 2412513.

Among the starting compounds (III), (V) and (XI) in the present invention, novel compounds can be prepared by the conventional processes which are illustrated by the following schemes.

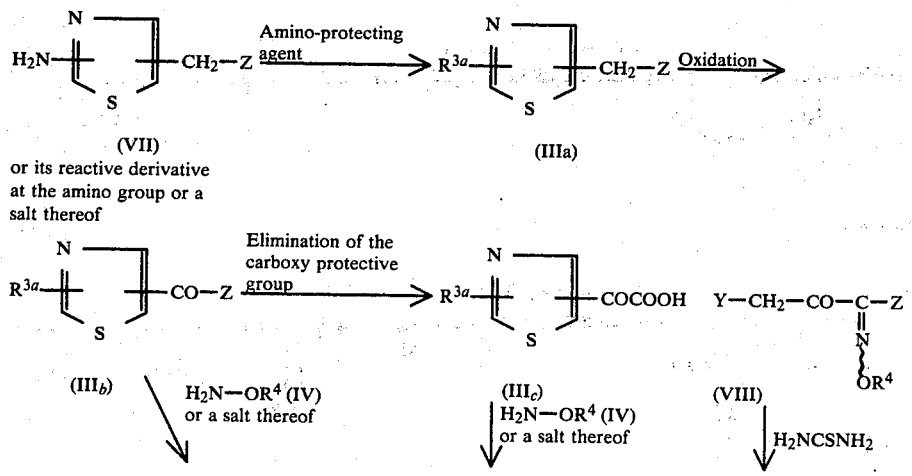

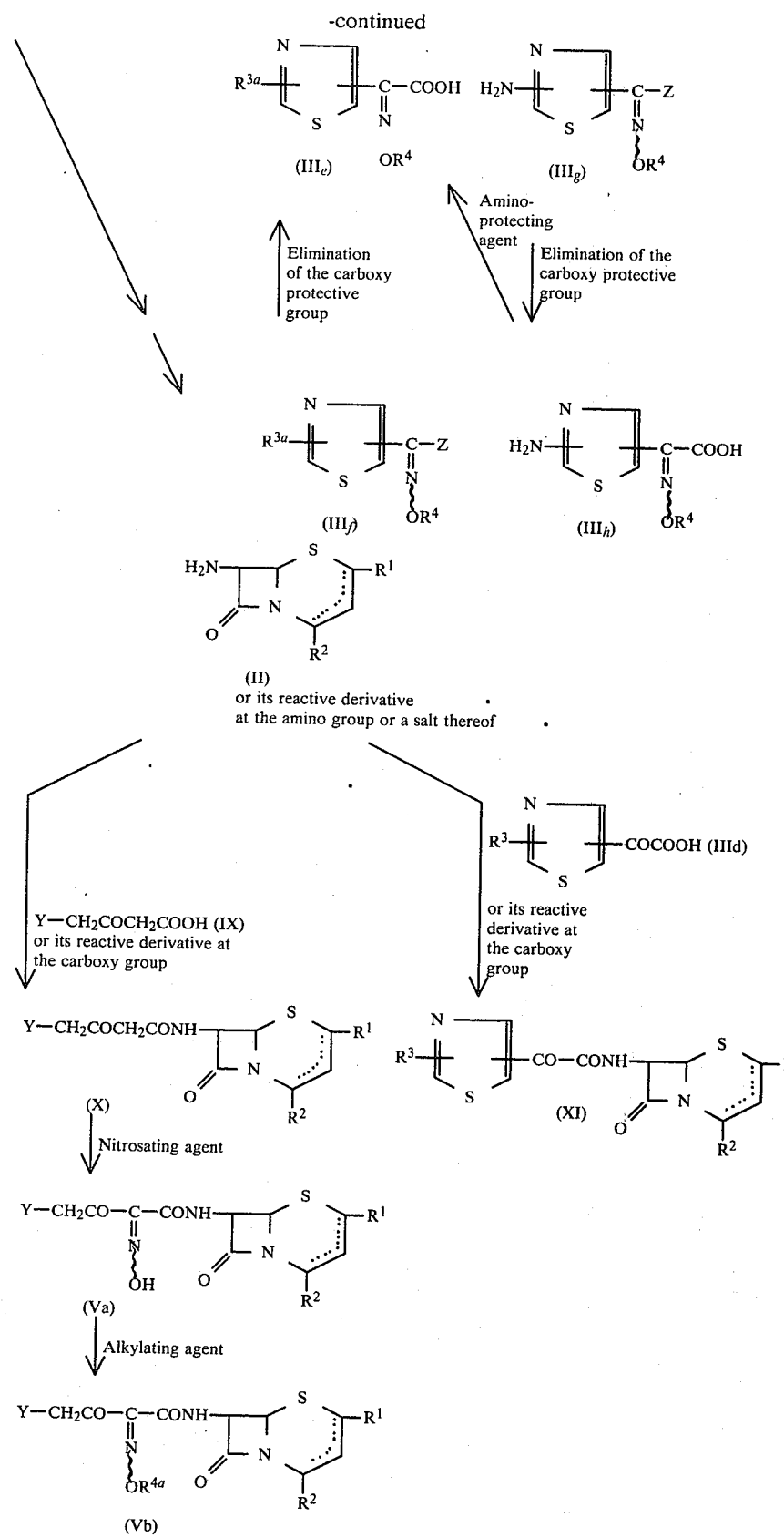
wherein $R^1$, $R^2$, $R^{2a}$, $R^3$, $R^{3a}$, $R^4$, $R^{4a}$ and Y are each as defined above, and
Z is a protected carboxy group.
Regarding the object compounds (I) and (Ia)–(Ij) and the starting compounds (III), (IIIa)–(IIIh), (VII) and (XI), it is to be understood that they include tautomeric isomers. That is, in case that the group of the formula:

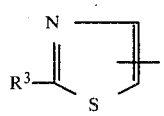

($R^3$ is as defined above) is contained in the molecules of said object and starting compounds, said group of the formula can be also alternatively represented by its tautomeric formula:

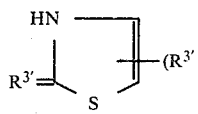

is imino or a protected imino group). That is, the both of said groups are in the state of equilibrium each other and such tautomerism can be represented by the following equilibrium.

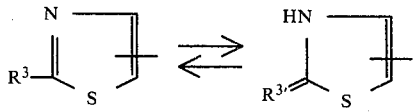

wherein $R^3$ and $R^{3'}$ are each as defined above.

These types of tautomerism between the amino-compound and the corresponding imino-compound as stated above have been well known in the literature, and it is obvious to be skilled in the arts that both of the tautomeric isomers are easily convertible reciprocally and are included within the same category of the compound per se. Accordingly, the both of the tautomeric forms of the object compounds (I) and (Ia)–(Ij) and the starting compound (III), (IIIa)–(IIIh), (VII) and (XI) are clearly included within the scope of the present invention. In the present specification and claims, the object and starting compounds including the group of such tautomeric isomers are represented by using one of the expressions therefor, that is the formula:

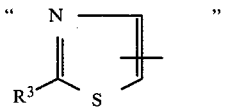

only for the convenient sake.

Furthermore, regarding the object compounds (I), (Ia)–(Ib) and (Ie)–(Ij) and the starting compounds (III), (IIIe)–(IIIh), (V), (Va)–(Vb) and (VIII), it is to be understood that said object and starting compounds include syn isomer, anti isomer and a mixture thereof. That is, in case that the hydroxyimino or lower alkoxyimino group is contained in the molecules of said object and starting compounds, said object and starting compounds can be optionally obtained as syn isomer or anti isomer or a mixture thereof. Accordingly, in this specification, syn isomer means one geometrical isomer having the partial structure represented by the following formula:

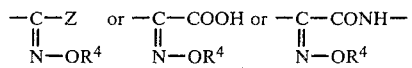

and anti isomer means the other geometrical isomer having the partial structure represented by the following formula:

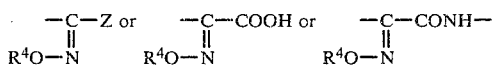

wherein $R^4$ and Z are each as defined above.

Suitable pharmaceutically acceptable salts of the object compounds (I) are conventional non-toxic salts and include a metal salt such as an alkali metal salt (e.g., sodium salt, potassium salt, etc.) and an alkaline earth metal slat (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylenediamine salt, etc.), an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable lower alkyl may include methyl, ethyl, propyl, isopropyl, butyl, pentyl, heyxl and the like.

Suitable protected carboxy may include an esterified carboxy and the like, and suitable examples of the ester moiety in said esterified carboxy may be the ones such as lower alkyl ester (e.g., methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower)alkyl ester (e.g., acetoxymethyl ester, propionyloxymethyl ester, butyryloxymethyl ester, valeryloxymethyl ester, pivaloyloxymethyl ester, 2-acetoxyethyl ester, 2-propionyloxyethyl ester, hexanoyloxymethyl ester etc.);

lower alkanesulfonyl(lower)alkyl ester (e.g., 2-mesylethyl ester, etc.) or mono(or di or tri)-halo(lower)alkyl ester (e.g., 2-iodoethyl ester, 2,2,2-trichloroethyl ester, etc.);

lower alkenyl ester (e.g., vinyl ester, allyl ester, etc.);

lower alkynyl ester (e.g., ethynyl ester, propynyl ester, etc.);

ar(lower)alkyl ester which may have at least one suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);

aryl ester which may have at least one suitable substituent(s) (e.g., phenyl ester, 4-chlorophenyl ester, tolyl ester, tertiarybutylphenyl ester, xylyl ester, mesityl ester, cumenyl ester, etc.), and the like.

Suitable protected amino may include an amino group substituted by a conventional protecting group such as acyl as mentioned below, ar(lower)alkyl which may have at least one suitable substituent(s) (e.g., benzyl, 4-methoxybenzyl, phenethyl, trityl, 3,4-dimethoxybenzyl, etc.) or the like.

Suitable acyl may include carbamoyl, aliphatic acyl group and acyl group containing an aromatic or heterocyclic ring. And, suitable examples of the said acyl may be lower alkanoyl (e.g., fomyl, acetyl, propionyl, butyryl, isobutyryl, valeryl, isovaleryl, oxalyl, succinyl, pivaloyl, etc.);

lower alkoxycarbonyl (e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g., mesyl, ethanesulfonyl, propanesulfonyl, isopropanesulfonyl, butanesulfonyl, etc.);

arnesulfonyl (e.g., benzenesulfonyl, tosyl, etc.);

aroyl (e.g., benzoyl, toluoyl, naphthoyl, phthaloyl, indancarbonyl, etc.);

ar(lower)alkanoyl (e.g., phenylacetyl, phenylpropionyl, etc.);

ar(lower)alkoxycarbonyl (e.g., benzyloxycarbonyl, etc.), and the like.

The acyl moiety as stated above may have at least one suitable substituent(s) such as halogen (e.g., chlorine, bromine, iodine or fluorine), cyano, lower alkyl (e.g., methyl, ethyl, propyl, isopropyl, butyl, etc.), lower alkenyl (e.g., vinyl, allyl, etc.), or the like, suitable examples of which may be mono(or di or tri)halo(lower)alkanoyl (e.g., trifluoroacetyl, etc.).

Suitable lower alkylene moiety in the terms "hydroxyimino(lower)alkylene" and "lower alkoxyimino(lower)alkylene" may include methylene, ethylene, trimethylene, propylene, tetramethylene and the like.

Suitable lower alkoxy moiety in the term "lower alkoxyimino(lower)alkylene" may include methoxy, ethoxy, propoxy, isopropoxy, butoxy, isobutoxy, pentyloxy, hexyloxy and the like.

Suitable ester moiety of an esterified carboxy may include the ester exemplified for protected carboxy.

Suitable residue of an acid may include halogen (e.g., chlorine, bromine, iodine or fluorine) and the like.

The various processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as acetoacetic acid or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester dimethyliminomethyl [(CH$_3$)$_2$N+=CH-] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can be optionally selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvents may be also used in a mixture with water.

When the compound (III) is used in free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)-carbodiimide, N,N-carbonylbis-(2-methylimidazole), pentamethyleneketene-N-cyclohexylimine, diphenylketene-N-cyclohexylimine, ethoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)-isoxazolium hydroxide intra-molecular salt, (chloromethylene)dimethylammonium chloride, 1-(p-chlorobenzenesulfonyloxy)-6-chloro-1H-benzotriazole, or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

It is to be noted that, in order to prepare a syn isomer of the object compound (I) selectively and in high yield, it is advisable and preferable to select a suitable condition. For example, a syn isomer of the object compound (I) can be obtained selectively and in high yield by conducting the present invention of the compound (II) with the corresponding syn isomer of the starting compound (III) in the presence of a Vilsmeier reagent such as the one prepared from dimethylformamide and phosphorus oxychloride or the like. Especially, a syn isomer of the object compound (I) wherein $R^3$ is amino can be obtained in good results by conducting the present reaction in the presence of more than two molar equivalents of phosphorus oxychloride to each amount of the corresponding syn isomer of the starting compound (III), wherein $R^3$ is amino, and dimethylformamide, and more preferable results can be achieved by conducting a step of activation of the syn isomer of the starting compound (III) wherein $R^3$ is amino in the presence of a silyl compound such as bis(trimethylsilyl)acetamide, trimethylsilylacetamide or the like.

Process 2

The object compound ($I_a$) or a salt thereof can be prepared by subjecting the compound ($I_b$) or a salt thereof to elimination reaction of the amino protective group.

Suitable salt of the compound ($I_b$) can be referred to the metal salt, ammonium salt and organic amine salt exemplified for the compound (II).

The elimination reaction is carried out in accordance with a conventional method such as hydrolysis, reduction, or the ike. The hydrolysis may also include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, cycloalkoxycarbonyl, substituted or unsubstituted aralkoxycarbonyl, aralkyl (e.g., trityl), substituted phenylthio, substituted aralkylidene, substituted alkylidene, substituted cycloalkylidene or the like. Suitable acid includes an organic or inorganic acid such as formic acid, trifluoroacetic acid, benzenesulfonic acid, p-toluenesulfonic acid, hydrochloric acid and the like, and the most suitable acid is an acid which can be easily removed from the reaction mixture by a conventional manner such as distillation under reduced pressure, for example, formic acid, trifluoroacetic acid, etc. The acids can be selected according to the kind of the protected group to be eliminated. When the elimination reaction is conducted with an acid, it can be carried out in the presence or absence of a solvent. Suitable solvent includes water, a conventional organic solvent or a mixture thereof. The hydrolysis using hydrazine is commonly applied for eliminating a phthaloyl type amino-protective group.

The reductive elimination is generally applied for eliminating the protective group, for example, haloalkoxycarbonyl (e.g., trichloroethoxycarbonyl, etc.), substituted or unsubstituted aralkoxy carbonyl (e.g., benzyloxycarbonyl, etc.), 2-pyridylmethoxycarbonyl, etc. Suitable reduction may include, for example, reduction with an alkali metal borohydride (e.g., sodium borohydride, etc.), reduction with a combination of a metal (e.g., tin, zinc, iron, etc.) or the said metal together with a metal salt compound (e.g., chromous chloride, chromous acetate, etc.) and an organic or inorganic acid (e.g., acetic acid, prpionic acid, hydrochloric acid, etc.); and catalytic reduction. Suitable catalyst includes a conventional one, for example, Raney nickel, platinum oxide, palladium on charcoal and the like.

Among the protective groups, the acyl group can be generally eliminated by hydrolysis. Especially, trifluoroacetyl group can be easily eliminated by treating with water even in around neutral condition, and halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g., phosphorus oxychloride, etc.) and an iminoetherifying agent such as lower alkanol (e.g., methanol, ethanol, etc.), if necessary, followed by hydrolysis.

The reaction temperature is not critical and may be suitably selected in accordance with the kind of the protective group for the amino group and the elimination method as mentioned above, and the reaction is preferably carried out under a mild condition such as under cooling or at slightly elevated temperature.

The present invention includes, within its scope, the cases that the protected carboxy is transformed into the free carboxy group during the reaction or the posttreating step of the present process.

Process 3

The object compound ($I_c$) or a salt thereof can be prepared by reacting the compound (XI) or a salt thereof with the compound (IV) or a salt thereof.

Suitable salt of the compound (XI) can be referred to ones exemplified for the compound (II), and suitable salt of the compound (IV) may include an inorganic acid salt (e.g., hydrochloride, hydrobromide, sulfate, etc.), an organic acid salt (e.g., acetate, maleate, p-toluenesulfonate, etc.) and the like.

The present reaction is usually carried out in a solvent such as water, an alcohol (e.g., methanol, ethanol, etc.) or any other solvent which does not adversely influence the present reaction.

The present reaction is preferably carried out in the presence of a base, for example, an inorganic base such as alkali metal (e.g., sodium, potassium, etc.), alkaline earth metal (e.g., magnesium, calcium, etc.), the hydroxide or carbonate or bicarbonate thereof or the like, and an organic base such as alkali metal alkoxide (e.g., sodium methoxide, sodium ethoxide, etc.), trialkylamine (e.g., trimethylamine, triethylamine, etc.), N,N-dialkylaniline (e.g., N,N-dimethylaniline, etc.), pyridine or the like.

The reaction temperature is not critical and the reaction is usually carried out under cooling to heating.

Process 4

The object compound ($I_e$) or a salt thereof can be prepared by reacting the compound (V) or a salt thereof with the compound (VI).

Suitable salt of the compound (V) can be referred to the ones exemplified for the compound (II).

The present reaction is usually carried out in a solvent such as water, an alcohol (e.g., methanol, ethanol, etc.), benzene, dimethylformamide, tetrahydrofuran or any other solvent which does not adversely influence the reaction.

The reaction temperature is not critical and the reaction is usually carried out from at ambient temperature to under heating.

Process 5

The object compound ($I_f$) or a salt thereof can be prepared by reacting the compound ($I_g$) or a salt thereof with an alkylating agent.

Suitable salt of the compound ($I_g$) can be referred to the ones exemplified for the compound (II).

Suitable alkylating agent used in the present reaction may include di(lower)alkyl sulfate (e.g., dimethyl sulfate, diethyl sulfate, etc.), diazo(lower)alkane (e.g., diazomethane, diazoethane, etc.), lower alkyl halide (e.g., methyl iodide, ethyl iodide, ethyl bromide, etc.), lower alkyl sulfonate (e.g., methyl p-toluenesulfonate, etc.), and the like.

The reaction using diazo-(lower)alkane is usually carried out in a solvent such as diethyl ether, dioxane or any other solvent which does not adversely influence the reaction under cooling or at ambient temperature.

The reaction using other alkylating agent is usually carried out in a solvent such as water, acetone, ethanol, diethyl ether, dimethylformamide or any other solvent which does not adversely influence the reaction under cooling to heating, and the reaction is preferably carried out in the presence of a base such as an inorganic base or an organic base as aforementioned.

Process 6

The object compound ($I_h$) or a salt thereof can be prepared by subjecting the compound ($I_i$) or a salt thereof to elimination reaction of the carboxy protective group.

Suitable salt of the compound ($I_i$) can be referred to the acid addition salt exemplified for the compound (II).

In the present elimination reaction, all conventional methods used in the elimination reaction of the carboxy protective group, for example, hydrolysis, reduction, etc. are applicable.

When the carboxy protective group is an ester, it can be eliminated by hydrolysis. The hydrolysis is preferably carried out in the presence of a base or an acid.

Suitable base may include an inorganic base and an organic base as aforementioned in Process 2.

Suitable acid may include an organic acid (e.g., formic acid, acetic acid, propionic acid, etc.) and an inorganic acid (e.g., hydrochloric acid, hydrobromic acid, sulfuric acid, etc.). The reduction can be applicable to elimination of the protective group such as 2-iodoethyl ester, 2,2,2-trichloroethyl ester, or the like. The reduction applicable to the elimination reaction of the present invention may include, for example, reduction using a combination of a metal (e.g., zinc, zinc amalgam, etc.) or a chrome salt compound (e.g., chromous chloride, chromous acetate, etc.) and an organic or inorganic acid (e.g., acetic acid, propionic acid, hydrochloric acid, etc.), and reduction in the presence of a metallic catalyst. The metallic catalysts for the catalytic reduction include, for example, platinum catalyst (e.g., platinum wire, spongy platinum, platinum black, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), and the like.

The reaction temperature is not critical, and it may be suitably selected in accordance with the kind of the protective group of the carboxy and the elimination method.

Process 7

The object compound ($I_j$) or a salt thereof can be prepared by subjecting the compound ($I_h$) or a salt thereof to esterification reaction.

Suitable salt of the compound ($I_h$) can also be referred to the ones exemplified for the compound (II).

The esterifying agent to be used in the present reaction may be a compound of the formula:

$$X-R^5 \qquad (XI)$$

where in $R^5$ is as defined above and X is hydroxy or reactive derivatives thereof.

A suitable example of the reactive derivative of hydroxy may include a residue of an acid as aforementioned.

The present reaction is usually carried out in a solvent such as dimethylformamide, pyridine, hexamethylphosphoric triamide, dioxane or other solvents which does not adversely affect the reaction.

In case that the compound ($I_h$) is used in a form of free acid, the reaction is preferably carried out in the presence of a base such as an inorganic base or an organic base as aforementioned in Process 2.

The reaction temperature is not critical and the reaction is preferably carried out under cooling, at ambient temperature or under warming.

In the aforementioned reactions and/or the posttreating steps of the processes of the present invention, the aforementioned tautomeric isomers may occasionally transformed into the other tautomeric isomers, and such cases are also included in the scope of the present invention.

In the aforementioned reactions and/or the posttreating steps of the processes of the present invention, the aforementioned syn or anti isomer may occasionally transformed into the other isomer partially or wholly, and such cases are also included in the scope of the present invention.

In case that the object compound (I) is obtained in a form of the free acid at 4 position and/or in case that the object compound (I) has a free amino group, it may be transformed into its pharmaceutically acceptable salt as aformentioned by a conventional method.

Processes for the preparation of the starting compounds are explained in detail as follows.

The starting compound ($III_a$) can be prepared by reacting the compound (VII) or its reactive derivative at the amino group or a salt thereof with an amino-protecting agent, and the starting compound ($III_e$) can be prepared by reacting the compound ($III_h$) or its reactive derivative at the amino group or a salt thereof with an amino-protecting agent, respectively.

Suitable reactive derivative at the amino group of the compounds (VII) and ($III_h$) and suitable salt of the compounds (VII) and ($III_h$) may include the same ones as illustrated in the explanations of the reactive derivative at the amino group of the compound (II) and salt of the compound (II), respectively.

Suitable amino-protecting agent may include acylating agent and the like.

Suitable acylating agent may include an aliphatic, aromatic and heterocyclic isocyanate, and the corresponding isothiocyanate, and an aliphatic, aromatic and heterocyclic carboxylic acid, and the corresponding sulfonic acid, carbonic acid ester and carbamic acid, and the corresponding thio acid, and the reactive derivative of the above acids.

Suitable reactive derivative of the above acids may include the same ones as illustrated in the explanation of "reactive derivative at the carboxy group of the compound (III)". The example of the protective group to be introduced into the amino group in the compounds (VII) and (III$_h$) with the above amino-protecting agent may be the same ones as illustrated in the explanation of the protective group in the terms "a protected amino group".

The present reaction is carried out in the similar manner as illustrated in the reaction of the compound (II) or its reactive derivative at the amino group or a salt thereof with the compound (III) or its reactive derivative at the carboxy group.

The starting compound (III$_b$) can be prepared by oxidizing the compound (III$_a$).

The present oxidation reaction is conducted by a conventional method which is applied to the transformation of so-called activated methylene group into carbonyl group. That is, the present oxidation is conducted by a method, for example, by using a conventional oxidizing agent such as selenium dioxide, trivalent manganese compound (e.g. manganous acetate and potassium permanganate, etc.) or the like. The present oxidation is usually carried out in a solvent which does not adversely influence the reaction, for example, water, dioxane, tetrahydrofuran, and the like.

The reaction temperature is not critical and the reaction is preferably carried out under warming to heating.

The starting compound (III$_c$) can be prepared by subjecting the compound (III$_b$) to elimination reaction of the carboxy protective group, the starting compound (III$_e$) can be prepared by subjecting the compound (III$_f$) to elimination reaction of the carboxy protective group, and the starting compound (III$_h$) can be prepared by subjecting the compound (III$_g$) to elimination reaction of the carboxy protective group, respectively.

The elimination reaction is carried out in the similar manner to that illustrated for the elimination reaction of Process 6.

The starting compound (III$_e$) can be prepared by reacting the compound (III$_c$) with the compound (IV) or a salt thereof, and the starting compound (III$_f$) can be prepared by reacting the compound (III$_b$) with the compound (IV) or a salt thereof, respectively.

The present reaction is carried out in the similar manner to that illustrated in the reaction of Process 3.

The starting compound (III$_g$) can be prepared by reacting the compound (VIII) with thiourea.

The present reaction is carried out in the similar manner to that illustrated in the reaction of Process 4.

The compound (X) and the starting compound (XI) can be prepared by reacting the compound (II) or its reactive derivative at the amino group or a salt thereof with the corresponding compounds (IX) and (IIId) or their reactive derivative at the carboxy group, respectively.

Suitable reactive derivative at the carboxy group of the compounds (IX) and (IIId) may include the same ones as illustrated in the explanation of "reactive derivative at the carboxy group of the compound (III)".

The present reaction is carried out in the similar manner to that illustrated in the reaction of Process 1.

The starting compound (V$_a$) can be prepared by reacting the compound (X) with a nitrosating agent.

Suitable nitrosating agent may include nitrous acid, alkali metal nitrite (e.g., sodium nitrite, etc.), lower alkyl nitrite (e.g., amyl nitrite etc.) and the like.

The present reaction is usually carried out in a solvent such as water, acetic acid, benzene, methanol, ethanol or any other solvent which does not adversely influence the reaction.

The reaction temperature is not critical and the reaction is usually carried out under cooling or at ambient temperature.

The starting compound (V$_b$) can be prepared by reacting the compound (V$_a$) with an alkylating agent.

The present reaction is carried out in the similar manner to that illustrated in the reaction of Process 5.

The object compounds (I) and pharmaceutically acceptable salt thereof of the present invention exhibit high antibacterial activity and inhibit the growth of a number of microorganisms including Gram-positive and Gram-negative bacteria. Especially, the syn isomers of the object compounds (I) and pharmaceutically acceptable salt thereof exhibit generally much higher antibacterial activity than that of the corresponding anti isomers of the object compounds (I) and pharmaceutically acceptable salt thereof. For therapeutic purpose, the compounds according to the present invention can be used in the form of pharmaceutical preparation which contain said compounds, as an active ingredient, in admixture with a pharmaceutically acceptable carriers such as an organic or inorganic solid or liquid excipient suitable for oral, parenteral or external administration. The pharmaceutical preparations may be capsules, tablets, dragees, ointments or suppositories, solutions, suspensions, emulsions, and the like. If desired, there may be included in the above preparations auxiliary substances, stabilizing agents, wetting or emulsifying agents, buffers and other commonly used additives.

While the dosage of the compounds will vary depend upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria.

In order to illustrate the usefulness of the object compounds, anti-microbial activities of some representative compounds of the present invention against some test strains of pathogenic bacteria are shown in their minimal inhibitory concentrations below.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml. after incubation at 37° C. for 20 hours.

Test compounds (1) 2-Methyl-7-[2-methoxyimino-2-(2-aminothiazol-4-yl)acetamido]-3-cephem-4-carboxylic acid (syn isomer) (Test compound (1))

(2) Pivaloyloxymethyl 2-methyl-7-[2-methoxyimino-2-(2-aminothiazol-4-yl)acetamido]-3-cephem-4-carboxylate (syn isomer) (Test compound (2))

Test Results:

| Organism | | Test compound(1) | Test compound(2) |
|---|---|---|---|
| E. coli | No. 324 | 0.05 | 0.2 |
| | No. 341 | 0.2 | 0.78 |
| Kl. aerogenes | No. 417 | 0.2 | 0.2 |
| | No. 418 | 0.1 | 0.78 |
| | No. 427 | 0.05 | 0.2 |
| | No. 428 | 0.2 | 1.56 |
| Pr. minabilis | No. 501 | 0.05 | 0.2 |
| | No. 520 | 0.05 | 0.1 |
| | No. 525 | 0.05 | 0.2 |

The present invention is illustrated by the following examples.

PREPARATION OF THE STARTING COMPOUNDS

Preparation 1

(a) A mixture of 2,2,2-trichloroethyl 2-methyl-7-amino-3-cephem-4-carboxylate hydrochloride (0.38 g.), trimethylsilylacetamide (1.1 g.) and methylene chloride (10 ml.) was stirred for 30 minutes at room temperature, and thus obtained solution was cooled to $-15°$ C. To the solution was added dropwise 3-oxo-4-bromobutyryl bromide (1.0 m mole) in carbon tetrachloride (13 ml.) under cooling to $-15°$ C., and the mixture was stirred for 1.5 hours at the same temperature and for 30 minutes without external cooling. The mixture was poured into cold water, and then the organic layer was separated therefrom. The organic layer was washed with 2 N hydrochloric acid (8 ml×3) and water (10 ml×2) in turn, dried over magnesium sulfate and then filtered. The filtrate was concentrated under reduced pressure.

The residue was pulverized in diisopropyl ether, collected by filtration and then dried to give pale brown powder of 2,2,2-trichloroethyl 2-methyl-7-(3-oxo-4-bromobutyramido)-3-cephem-4-carboxylate (0.31 g.), mp 78° to 83° C. (dec.).

I.R. Spectrum (Nujol)
3320, 1785, 1735, 1675, 1284, 1210 cm$^{-1}$
N.M.R. Spectrum (CDCl$_3$, δ)
1.54 (3H, d, J=7 Hz)
3.65 (1H, m)
3.76 (4/5H, s)
4.11 (6/5H, s)
4.90 (2H, s)
5.00 (1H, d, J=6 Hz)
5.95 (1H, m)
6.72 (1H, d, J=6.8 Hz)
7.05 (2/5H, d, J=9 Hz)
7.73 (3/5H, d, J=9 Hz)

Similarly, the following compound was obtained.
p-Nitrobenzyl 2-methyl-7-(3-oxo-4-bromobutyramido)-3-cephem-4-carboxylate, powder.
I.R. Spectrum (Nujol)
3270, 1780, 1725, 1655, 1625, 1600 cm$^{-1}$
N.M.R. Spectrum (d$_6$-dimethylsulfoxide, δ)
ppm 1.79 (3H, d, J=6.5 Hz)
3.67 (2H, s)
3.7-4.2 (1H, m)
4.43 (2H, s)
5.13 (1H, d, J=4.5 Hz)
5.43 (2H, s)
5.87 (1H, dd, J=4.5 and 8 Hz)
6.76 (1H, d, J=6.5 Hz)
7.73 (2H, d, J=9 Hz)
8.26 (2H, d, J=9 Hz)
9.13 (1H, d, J=8 Hz)

(b) To a solution of 2,2,2-trichloroethyl 2-methyl-7-(3-oxo-4-bromobutyramido)-3-cephem-4-carboxylate (2.54 g.) in glacial acetic acid (25 ml.) was added dropwise a solution of sodium nitrite hydrate (0.33 g.) in water (1 ml.) over 3 minutes with stirring at 10° to 15° C., and then the mixture was stirred for 1 hour at the same temperature. After the reaction mixture was poured into cold water (70 ml.), the precipitates were collected by filtration and then dried to give brown powder of 2,2,2-trichloroethyl 2-methyl-7-(2-hydroxyimino-3-oxo-4-bromobutyramido)-3-cephem-4-carboxylate (a mixture of syn and anti isomers) (2.0 g.), mp 76° to 80° C. (dec.).

I.R. Spectrum (Nujol)
1670-1710, 1540, 1280, 1215, 715 cm$^{-1}$
N.M.R. Spectrum (d$_6$-dimethylsulfoxide, δ)
1.44 (3H, d, J=7 Hz)
3.2-3.8 (2H, broad)
3.91 (1H, m)
4.57 (1H, s)
5.02 (2H, s)
5.16 (1H, d, J=5 Hz)
5.91 (1H, dd, J=5 and 9 Hz)
6.74 (1H, d, J=6.5 Hz)
9.32 (1H, d, J=9 Hz)
Similarly, the following compound was obtained.
p-Nitrobenzyl 2-methyl-7-(2-hydroxyimino-3-oxo-4-bromobutyramido)-3-cephem-4-carboxylate (syn isomer).
I.R. Spectrum (Nujol)
3260, 1775, 1725, 1700, 1660, 1630, 1600 cm$^{-1}$
N.M.R. Spectrum (d$_6$-dimethylsulfoxide, δ)
ppm 1.45 (3H, d, J=7 Hz)
3.6-4.2 (1H, m)
4.60 (2H, s)
5.17 (1H, d, J=5 Hz)
5.43 (2H, s)
5.98 (1H, dd, J=5 and 9 Hz)
6.77 (1H, d, J=7 Hz)
7.73 (2H, d, J=9 Hz)
8.27 (2H, d, J=9 Hz)
9.37 (1H, d, J=9 Hz)
13.32 (1H, s)

Preparation 2

To a solution of 2,2,2-trichloroethyl 2-methyl-7-(2-hydroxyimino-3-oxo-4-bromobutyramido)-3-cephem-4-carboxylate (a mixture of syn and anti isomers) (1.2 g.) in ethanol (20 ml.) was added dropwise a solution of diazomethane (0.1 mole) in diethyl ether under stirring and ice-cooling to complete the reaction. After the reaction mixture was concentrated under reduced pressure, the residue was pulverized in diisopropyl ether, collected by filtration and then dried to give brown powder of 2,2,2-trichloroethyl 2-methyl-7-(2-methoxyimino-3-oxo-4-bromobutyramido)-3-cephem-4-carboxylate (a mixture of syn and anti isomers) (1.1 g.), mp 80° to 83° C. (dec.).

I.R. Spectrum (Nujol)
3300, 1785, 1737, 1650-1710, 1535, 1280, 1210, 1160, 1045, 715 cm$^{-1}$
N.M.R. Spectrum (d$_6$-dimethylsulfoxide, δ)
1.46 (3H, d, J=7 Hz)

4.0 (1H, m)
4.04 (3H, s)
4.62 (1H, s)
5.05 (2H, s)
5.29 (1H, d, J=5 Hz)
5.95 (1H, m)
6.74 (1H, m)
9.48 (1H, d, J=9 Hz)

Preparation 3

(a) To acetic anhydride (384 ml.) was added dropwise formic acid (169.2 ml.) over 15 to 20 minutes under cooling below 35° C., and the mixture was stirred for 1 hour at 55° to 60° C. To the mixture was added ethyl 2-(2-aminothiazol-4-yl)acetate, which can be represented as ethyl 2-(2-imino-2,3-dihydrothiazol-4-yl)acetate, (506 g.) over 15 to 20 minutes under ice-cooling and stirring, and then the mixture was stirred for 1 hour at room temperature. After the reaction, the solvents were distilled off. To the residue was added diisopropyl ether (2500 ml.), and the mixture was stirred for 1 hour at room temperature. The precipitates were collected by filtration, washed with diisopropyl ether and then dried to give ethyl 2-(2-formylaminothiazol-4-yl)acetate, which can be represented as ethyl 2-(2-formylimino-2,3-dihydrothiazol-4-yl)acetate, (451.6 g.), mp 125° to 126° C. The remaining filtrate was concentrated, and the residue was washed with diisopropyl ether (500 ml.) and then dried to give further the same object compound (78.5 g.).

I.R. Spectrum (Nujol)
1737, 1700 cm$^{-1}$
N.M.R. Spectrum (CDCl$_3$, δ)
1.25 (3H, t, J=8 Hz)
3.7 (2H, s)
4.18 (2H, q, J=8 Hz)
6.9 (1H, s)
8.7 (1H, s)

(b) A mixture of manganous acetate tetrahydrate (120 g.), acetic acid (1000 ml) and acetic anhydride (100 ml.) was stirred for 20 minutes in an oil bath heated at 130° to 135° C., and to the mixture was added potassium permanganate (20 g.) over 5 minutes at 105° to 110° C. with stirring and then the mixture was further stirred for 30 minutes at 130° to 135° C. The mixture was cooled to room temperature, and to the mixture was added ethyl 2-(2-formylaminothiazol-4-yl)acetate, which can be represented as ethyl 2-(2-formylimino-2,3-dihydrothiazol-4-yl)acetate, (53.5 g.), and then the mixture was stirred for 15 hours at 38° to 40° C. under introduction of air at the rate of 6000 ml. per minute. After the reaction, the precipitates were collected by filtration. The precipitates were washed with acetic acid and water in turn and then dried to give ethyl 2-(2-formylaminothiazol-4-yl)glyoxylate, which can be represented as ethyl 2-(2-formylimino-2,3-dihydrothiazol-4-yl)glyoxylate, (41.5 g.), mp 232° to 233° C. (dec.).

(c) To a suspension of ethyl 2-(2-formylaminothiazol-4-yl)glyoxylate, which can be represented as ethyl 2-(2-formylimino-2,3-dihydrothiazol-4-yl)glyoxylate, (281 g.) in water (1100 ml.) was added an 1 N sodium hydroxide aqueous solution (2.23 l.) under stirring and ice-cooling, and then the mixture was stirred for 5 minutes at 10° to 15° C. After the reaction mixture was filtered, the filtrate was adjusted to pH 1 with concentrated hydrochloric acid with stirring. The precipitates were collected by filtration, washed with water and then dried to give 2-(2-formylaminothiazol-4-yl)glyoxylic acid, which can be represented as 2-(2-formylimino-2,3-dihydrothiazol-4-yl)glyoxylic acid, (234 g.), mp 133° to 136° C. (dec.).

N.M.R. Spectrum (NaDCO$_3$, δ)
8.27 (1H, s)
8.6 (1H, s)

(d) To dimethylformamide (78 ml.) was added dropwise phosphorus oxychloride (11.9 g.) under stirring and icecooling, and the mixture was stirred for 30 minutes at 40° C. To the mixture was added 2-(2-formylaminothiazol-4-yl)glyoxylic acid, which can be represented as 2-(2-formylimino-2,3-dihydrothiazol-4-yl)glyoxylic acid, (7.8 g.) under cooling at −20° C., and then the mixture was stirred for 30 minutes under cooling at −20° to −15° C. Thus obtained mixture was added to a solution, which was prepared by stirring a mixture of 2-methyl-7-amino-3-cephem-4-carboxylic acid (8.35 g.) and bis(trimethylsilyl)acetamide (19.5 ml.) in dried methylene chloride (170 ml.) at room temperature, under cooling at −50° to −45° C. with stirring. The mixture was stirred for 1 hour at −45° to −40° C. and then the reaction mixture was poured into a solution of sodium bicarbonate (32 g.) in water (1.5 l) with shaking. The aqueous layer was separated and washed with ethyl acetate. The aqueous solution was layered with ethyl acetate and then adjusted to pH 1 to 2 with concentrated hydrochloric acid. The ethyl acetate layer was separated from the mixture, and the remaining aqueous layer was extracted with ethyl acetate (200 ml.×2). The ethyl acetate layers were combined together, washed with water and then concentrated to a small volume. The precipitates were collected by filtration, washed with a small amount of ethyl acetate and then dried to give 2-methyl-7-[2-(2-formylaminothiazol-4-yl)glyoxylamido]-3-cephem-4-carboxylic acid, which can be represented as 2-methyl-7-[2-(2-formylimino-2,3-dihydrothiazol-4-yl)glyoxylamido]-3-cephem-4-carboxylic acid, (7.9 g.), mp 210° to 215° C. (dec.).

I.R. Spectrum (Nujol)
3300, 3150, 1780, 1713, 1660, 1625, 1533 cm$^{-1}$
N.M.R. Spectrum (d$_6$-dimethylsulfoxide, δ)
1.45 (3H, d, J=7 Hz, 2—CH$_3$)
3.7-4.1 (1H, m, 2-H)
5.17 (1H, d, J=5 Hz, 6-H)
5.91 (1H, dd, J=5 and 8 Hz, 7—H)
6.59 (1H, d, J=6 Hz, 3—H)
8.40 (1H, s, 5—H on thiazole ring)
8.57 (1H, s, OHC—N=)
9.83 (1H, d, J=8 Hz, 7—CONH)

Preparation 4

(a) A solution of ethyl 2-methoxyimino-4-bromoacetoacetate (a mixture of syn and anti isomers) (17.4 g.) and thiourea (5.4 g.) in ethanol (100 ml.) was refluxed for 4 hours. The reaction mixture was allowed to stand in a refrigerator to precipitate crystals. The crystals were collected by filtration, washed with ethanol and dried to give ethyl 2-methoxyimino-2-(2-aminothiazol-4-yl)acetate hydrobromide (anti isomer) (9.5 g.). The filtrate and the washings were put together and concentrated under reduced pressure. Water (100 ml.) was added to the residue and the mixture was washed with ether.

The aqueous layer was alkalized with a 28% aqueous solution of ammonia and extracted with ethyl acetate. The extract was washed with water and a saturated aqueous sodium chloride solution and dried over magnesium sulfate. The solvent was distilled off under reduced pressure to give crystalline substance of ethyl 2-methoxyimino-2-(2-aminothiazol-4-yl)acetate (syn isomer), which can be represented as ethyl 2-methoxyimino-2-(2-imino-2, 3-dihydrothiazol-4-yl)acetate (syn isomer), (5.2 g.)

I.R. Spectrum (Nujol)
3400, 3300, 3150, 1725, 1630, 1559 cm$^{-1}$
N.M.R. Spectrum (CDCl$_3$, δ)
1.38 (3H, t, J=7 Hz)
4.03 (3H, s)
4.38 (2H, q, J=7 Hz)
5.91 (2H, broad s)
6.72 (1H, s)

(b) Ethanol (10 ml.) was added to a suspension of ethyl 2-methoxyimino-2-(2-aminothiazol-4-yl)acetate (syn isomer), which can be represented as ethyl 2-methoxyimino-2-(2-imino-2,3-dihydrothiazol-4-yl)acetate (syn isomer), (2.2 g.) in a 1 N aqueous solution of sodium hydroxide (12 ml.) and the mixture was stirred for 15 hours at ambient temperature. The reaction mixture was adjusted to pH 7.0 with 10% hydrochloric acid and ethanol was distilled off under reduced pressure. The residual aqueous solution was washed with ethyl acetate, adjusted to pH 2.8 with 10% hydrochloric acid and stirred under ice-cooling to precipitate crystals. The crystals were collected by filtration, washed with acetone and recrystallized from ethanol to give colorless needles of 2-methoxyimino-2-(2-aminothiazol-4-yl)acetic acid (syn isomer), which can be represented as 2-methoxyimino-2-(2-imino-2,3-dihydrothiazol-4-yl)acetic acid (syn isomer), (1.1 g.).

I.R. Spectrum (Nujol)
3150, 1670, 1610, 1585 cm$^{-1}$
N.M.R. Spectrum (d$_6$-dimethylsulfoxide, δ)
3.83 (3H, s)
6.85 (1H, s)
7.20 (2H, broad s)

Preparation 5

Pyridine (5 ml.) was added to a suspension of 2-methoxyimino-2-(2-aminothiazol-4-yl)acetic acid (syn isomer) which can be represented as 2-methoxyimino-2-(2-imino-2,3-dihydrothiazol-4-yl)acetic acid (syn isomer), (2.0 g.) in ethyl acetate (20 ml.). A solution of bis(2,2,2-trifluoroacetic)anhydride (2.5 g.) in ethyl acetate (3 ml.) was added dropwise thereto with stirring at 5° to 7° C. and the mixture was stirred for 30 minutes at 3° to 5° C. Water (30 ml.) was added to the reaction mixture and the ethyl acetate layer was separated. The aqueous layer was further extracted with ethyl acetate and two ethyl acetate layers were combined together, washed with water and a saturated aqueous sodium chloride solution and dried over magnesium sulfate. The solvent was distilled off under reduced pressure to give 2-methoxyimino-2-[2-(2,2,2-trifluoroacetylamino)-thiazol-4-yl]acetic acid (syn isomer), which can be represented as 2-methoxyimino-2-[2-(2,2,2-trifluoroacetylimino)-2,3-dihydrothiazol-4-yl]acetic acid (syn isomer), (0.72 g.).

I.R. Spectrum (Nujol)
1725, 1590 cm$^{-1}$
N.M.R. Spectrum (d$_6$-dimethylsulfoxide, δ)
3.91 (3H, s)
7.68 (1H, s)

Similarly, the following compound was obtained.

(i) 2-Methoxyimino-2-(2-formylaminothiazol-4-yl)acetic acid (syn isomer), which can be represented as 2-methoxyimino-2-(2-formylimino-2,3-dihydrothiazol-4-yl)acetic acid. (syn isomer), mp 152° C. (dec.).

I.R. Spectrum (Nujol)
3200, 2100–2800, 1950, 1600 cm$^{-1}$
N.M.R. Spectrum (d$_6$-dimethylsulfoxide, δ)
3.98 (1H, s)
7.62 (1H, s)
8.60 (1H, s)

EXAMPLE 1

To dimethylformamide (0.54 g.) was added dropwise phosphorus oxychloride (1.13 g.) under stirring and ice-cooling, and the mixture was stirred for 30 minutes at 40° C., and then dried ethyl acetate (13 ml.) was added thereto. To the mixture was gradually added 2-methoxyimino-2-(2-trifluoroacetylaminothiazol-4-yl)acetic acid (syn isomer), which can be represented as 2-methoxyimino-2-(2-trifluoroacetylimino-2,3-dihydrothiazol-4-yl)acetic acid (syn isomer), (2.0 g.) under cooling at 3° to 5° C., and the mixture was stirred for 40 minutes at the same temperature. Thus obtained solution was added to a solution, which was prepared by stirring a mixture of 2-methyl-7-amino-3-cephem-4-carboxylic acid (1.44 g.) and trimethylsilylacetamide (9.78 g.) in dried ethyl acetate (30 ml.) for 5 to 10 minutes at 35° to 40° C., under cooling at −25° to −20° C. with stirring. The mixture was stirred for 1 hour at the same temperature, and cold water was added thereto under ice-cooling, and then the mixture was stirred for about 5 minutes at the same temperature. The ethyl acetate layer was separated from the reaction mixture, and the remaining aqueous layer was extracted with ethyl acetate (20 ml. ×2). The ethyl acetate layers were combined together, washed with water and then water (50 ml.) was added thereto. The mixture was adjusted to pH 7.5 with a saturated aqueous solution of sodium bicarbonate, under ice-cooling and stirring, and the aqueous layer was separated therefrom. After washing the aqueous layer with ethyl acetate, ethyl acetate (70 ml.) was added thereto. The mixture was adjusted to pH 2.5 with 10% hydrochloric acid under ice-cooling and stirring. The ethyl acetate layer was separated from the mixture, and the remaining aqueous layer was extracted with ethyl acetate (30 ml.). The ethyl acetate layers were combined together, washed with an aqueous solution of sodium chloride, dried and then concentrated till the total volume became about 10 ml. To the residue was added diethyl ether (20 ml.) and the mixture was stirred for about 1 hour. The precipitates were collected by filtration, washed with diethyl ether and then dried to give 2-methyl-7-[2-methoxyimino-2-(2-trifluoroacetylaminothiazol-4-yl)acetamido]-3-cephem-4-carboxylic acid (syn isomer), which can be represented as 2-methyl-7-[2-methoxyimino-2-(2-trifluoroacetylimino-2,3-dihydrothiazol-4-yl)acetamido]-3-cephem-4-carboxylic acid (syn isomer), (2.2 g.), mp. 197° to 198° C. (dec.). The remaining filtrate was concentrated, and the residue was washed with diethyl ether and then dried to give the same object compound (0.3 g.).

I.R. Spectrum (Nujol)
3270, 1788, 1730, 1660 cm$^{-1}$
N.M.R. Spectrum (d$_6$-dimethylsulfoxide, δ)
1.46 (3H, d, J=8Hz, 2—CH$_3$)
3.7–4.0 (1H, m, 2—H)
3.95 (3H, s, OCH$_3$)
5.17 (1H, d, J=6Hz, 6—H)
5.94 (1H d,d, J=6 and 7Hz, 7—H)

6.62 (1H, d, J=6Hz, 3—H)
7.56 (1H, s, 5—H on thiazole ring)
9.81 (1H, d, J=7Hz, 7—CONH)

EXAMPLE 2

To dimethylformamide (6.42 g.) was added dropwise phosphorus oxychloride (12.5 g.) over 20 minutes with stirring under cooling to 5° to 10° C., and the mixture was stirred for 30 minutes at 40° C., and then ethyl acetate (200 ml.) was added thereto with vigorous stirring. After the mixture was cooled to 3° C., 2-methoxyimino-2-(2-formylaminothiazol-4-yl)acetic acid (syn isomer), which can be represented as 2-methoxyimino-2-(2-formylimino-2,3-dihydrothiazol-4-yl)acetic acid (syn isomer), (18.34 g.) was added thereto, and then the mixture was stirred for 40 minutes at 3° to 5° C. Thus obtained solution was added to a solution, which was prepared by stirring a mixture of 2-methyl-7-amino-3-cephem-4-carboxylic acid (17.1 g.) and trimethylsilylacetamide (84 g.) in ethyl acetate (300 ml.) for 1 hour at room temperature, with vigorous stirring under cooling to −25° C. The mixture was stirred for 1 hour at −20° to −15° C. and for 30 minutes at −10° to −5° C. To the mixture was added water (200 ml.) at room temperature, and the mixture was further stirred for 20 minutes at the same temperature. After a saturated aqueous sodium bicarbonate solution was added to the mixture in order to dissolve the precipitates, the aqueous layer was separated. To the aqueous layer was added ethyl acetate, and the mixture was adjusted to pH 2 with 2 N hydrochloric acid, and then the ethyl acetate layer was separated. The remaining aqueous layer was further extracted with ethyl acetate. The ethyl acetate layers were combined together, washed with a saturated aqueous sodium chloride solution, dried over magnesium sulfate, treated with an activated charcoal and then concentrated. Thus obtained crystalline residue was pulverized in diethyl ether, collected by filtration and then dried to give white crystals of 2-methyl-7-[2-methoxyimino-2-(2-formylaminothiazol-4-yl)acetamido]-3-cephem-4-carboxylic acid (syn isomer), which can be represented as 2-methyl-7-[2-methoxyimino-2-(2-formylimino-2,3-dihydrothiazol-4-yl)acetamido]-3-cephem-4-carboxylic acid (syn isomer), (32.2 g.). This compound was recrystallized from methanol to give white crystals of the pure object compound, mp 174° to 204° C. (dec.).

I.R. Spectrum (Nujol)
3270, 1780, 1655, 1285, 1040 cm$^{-1}$
N.M.R. Spectrum (d$_6$-dimethylsulfoxide, δ)
1.44 (3H, d, J=7Hz)
3.68–4.12 (1H, m)
3.90 (3H, s)
5.14 (1H, d, J=5Hz)
5.90 (1H, d, J=5Hz)
6.56 (1H, d, J=6Hz)
7.40 (1H, s)
8.50 (1H, s)

Similarly, the following compounds were obtained.
(1) 2-Methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), dp>241° C.
(2) 2,2,2-Trichloroethyl 2-methyl-7-[2-methoxyimino-2-(2-aminothiazol-4-yl)acetamido]-3-cephem-4-carboxylate (syn isomer), which can be represented as 2,2,2-trichloroethyl 2-methyl-7-[2-methoxyimino-2-(2-imino-2,3-dihydrothiazol-4-yl)acetamido]-3-cephem-4-carboxylate (syn isomer), mp 128° to 149° C. (dec.).
(3) Pivaloyloxymethyl 2-methyl-7-[2-methoxyimino-2-(2-aminothiazol-4-yl)acetamido]-3-cephem-4-carboxylate (syn isomer), which can be represented as pivaloyloxymethyl 2-methyl-7-[2-methoxyimino-2-(2-imino-2,3-dihydrothiazol-4-yl)acetamido]-3-cephem-4-carboxylate (syn isomer), mp 165° to 170° C. (dec.).

EXAMPLE 3

A suspension of 2-methoxyimino-2-(2-aminothiazol-4-yl)acetic acid (syn isomer), which can be represented as 2-methoxyimino-2-(2-imino-2,3-dihydrothiazol-4-yl)acetic acid (syn isomer), (26 g.) in ethyl acetate (250 ml.) was cooled to 5° C., and phosphorus oxychloride (25 g.) was added dropwise thereto with stirring under ice-cooling, and then the mixture was stirred for 30 minutes at 4° to 6° C. To the mixture was added dropwise a solution of trimethylsilylacetamide (22 g.) in ethyl acetate (20 ml.) with stirring under ice-cooling, and the mixture was stirred for 30 minutes at 4° to 6° C., and then phosphorus oxychloride (25 g.) was further added thereto with stirring under ice-cooling. The mixture was stirred for 15 minutes at the same temperature, and dimethylformamide (10.6 g.) was added dropwise thereto at the same temperature. The mixture was stirred for 40 minutes at the same temperature, and the resulting clear solution was cooled to −10° C. On the other hand, to a solution of 2-methyl-7-amino-3-cephem-4-carboxylic acid (23.9 g.) in a solution of sodium bicarbonate (25 g.) and water (400 ml.) was added acetone (300 ml.), and the mixture was cooled to −5° C. To the mixture was added dropwise the above prepared clear solution at −5° to 0° C., and then the mixture was stirred for 2 hours, all the while the mixture was kept to pH 6 with 15% aqueous sodium bicarbonate solution. Insoluble materials were filtered off, and the aqueous layer was separated. The aqueous layer was adjusted to pH 3 with 20% hydrochloric acid, and precipitated crystals were collected by filtration, washed with water and acetone in turn and then dried under reduced pressure to give 2-methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), (39.4 g.). This object compound was identified with the object compound prepared in Example 6 by IR and NMR determination.

The sodium or ammonium salt of this object compound can be obtained by a conventional manner, and physical properties of each compound are as follows.
(1) Sodium salt, powder.
IR Spectrum (Nujol): 1770, 1660, 1560, 1500 cm$^{-1}$
NMR Spectrum (d$_6$-dimethylsulfoxide, δ)
1.37 (3H, d, J=7.0 Hz)
3.64 (1H, m)
3.84 (3H, s)
4.97 (1H, d, J=5.0 Hz)
5.74 (1H, m)
6.21 (1H, d, J=6.0 Hz)
6.70 (1H, s)
7.30 (2H, m)
9.63 (1H, m)
(2) Ammonium salt, powder.
IR Spectrum (Nujol): 1775, 1660, 1580, 1530 cm$^{-1}$
NMR Spectrum (d$_6$-dimethylsulfoxide, δ)
1.37 (3H, d, J=7.0 Hz)

3.64 (1H, m)
3.83 (3H, s)
4.99 (1H, d, J=5.0 Hz)
5.8 (5H, m)
6.17 (1H, d, J=6.0 Hz)
6.87 (1H, s)
7.27 (2H, m)
9.55 (1H, m)

EXAMPLE 4

To a solution of sodium acetate (11.6 g.) in water (43 ml) was added 2-methyl-7-[2-methoxyimino-2-(2-trifluoroacetylaminothiazol-4-yl)acetamido]-3-cephem-4-carboxylic acid (syn isomer), which can be represented as 2-methyl-7-[2-methoxyimino-2-(2-trifluoroacetylimino-2,3-dihydrothiazol-4-yl)acetamido]-3-cephem-4-carboxylic acid (syn isomer), (2.1 g.) with stirring, and the mixture was adjusted to pH 6 with 5% aqueous sodium bicarbonate solution. The mixture was stirred overnight at room temperature. After the reaction, the reaction mixture was adjusted to pH 2.8 to 3 with 10% hydrochloric acid and then cooled. The precipitates were collected by filtration and then dried to give 2-methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), (1.1 g.), dp>241° C. The same object compound (0.25 g.) was further obtained from the filtrate by a conventional manner.

I.R. Spectrum (Nujol)
3470, 3320, 3190, 2380, 1783, 1690, 1655, 1622, 1530 cm$^{-1}$
N.M.R. Spectrum (d$_6$-dimethylsulfoxide, δ)
1.44 (3H, d, J=8Hz, 2—CH$_3$)
3.7–4.0 (1H, m, 2—H)
3.84 (3H, s, OCH$_3$)
5.12 (1H, d, J=6Hz, 6—H)
5.89 (1H, dd, J=6 and 8Hz, 7—H)
6.57 (1H, d, J=7Hz, 3—H)
6.77 (1H, s, 5—H on thiazole ring)
9.62 (1H, d, J=8Hz, 7—CONH)

EXAMPLE 5

To a suspension of 2-methyl-7-[2-methoxyimino-2-(2-formylaminothiazol-4-yl)acetamido]-3-cephem-4-carboxylic acid (syn isomer), which can be represented as 2-methyl-7-[2-methoxyimino-2-(2-formylimino-2,3-dihydrothiazol-4-yl)acetamido]-3-cephem-4-carboxylic acid (syn isomer), (9.0 g.) in methanol (90 ml.) was added concentrated hydrochloric acid (2.12 ml.) with stirring at room temperature, and the mixture was stirred for 7 hours at the same temperature. To the reaction mixture was gradually added diethyl ether till crystals started to precipitate. The mixture was allowed to stand for 30 minutes, and the precipitated crystals were collected by filtration, washed with diethyl ether and then dried to give white crystals of 2-methyl-7-[2-methoxyimino-2-(2-aminothiazol-4-yl)acetamido]-3-cephem-4-carboxylic acid hydrochloride (syn isomer), which can be represented as 2-methyl-7-[2-methoxyimino-2-(2-imino-2,3-dihydrothiazol-4-yl)acetamido]-3-cephem-4-carboxylic acid hydrochloride (syn isomer), (7.9 g.) The remaining filtrate was concentrated till the total volume became half. To the concentrated filtrate was gradually added diethyl ether till crystals started to precipitate, and the mixture was allowed to stand for 1 hour. The precipitated crystals were collected by filtration, washed with diethyl ether and then dried to give further the same object compound (0.5 g.).

I.R. Spectrum (Nujol)
3300, 3295, 1780, 1720, 1660, 1630, 1300 cm$^{-1}$
N.M.R. Spectrum (d$_6$-dimethylsulfoxide, δ)
1.44 (3H, d, J=7Hz)
3.70–4.14 (1H, m)
3.94 (3H, s)
5.10 (1H, d, J=5Hz)
5.84 (1H, d, J=5Hz)
6.59 (1H, d, J=6Hz)
6.94 (1H, s)

To a suspension of 2-methyl-7-[2-methoxyimino-2-(2-aminothiazol-4-yl)acetamido]-3-cephem-4-carboxylic acid hydrochloride (syn isomer), which can be represented as 2-methyl-7-[2-methoxyimino-2-(2-imino-2,3-dihydrothiazol-4-yl)acetamido]-3-cephem-4-carboxylic acid hydrochloride (syn isomer), (7.7 g.) in water (77 ml.) was added a saturated aqueous sodium bicarbonate solution (44 ml.). Thus obtained solution was adjusted to pH 3 with 1 N hydrochloric acid and then allowed to stand for 1 hour at cold place. The precipitated crystals were collected by filtration, washed with water and then dried to give white powder of 2-methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer) (6.67 g.), mp 196° to 240° C. (dec.).

I.R. Spectrum (Nujol)
3470, 3310, 3200, 1790, 1655, 1620, 1530, 1295, 1055 cm$^{-1}$
N.M.R. Spectrum (d$_6$-dimethylsulfoxide, δ)
1.48 (3H, d, J=8Hz)
3.65–4.08 (1H, m)
3.84 (3H, s)
5.10 (1H, d, J=5Hz)
5.84 (1H, d, J=5Hz)
6.54 (1H, d, J=6Hz)
6.72 (1H, s)

Similarly, the following compounds were obtained.

(1) 2,2,2-Trichloroethyl 2-methyl-7-[2-methoxyimino-2-(2-aminothiazol-4-yl)acetamido]-3-cephem-4-carboxylate (syn isomer), which can be represented as 2,2,2-trichloroethyl 2-methyl-7-[2-methoxyimino-2-(2-imino-2,3-dihydrothiazol-4-yl)acetamido]-3-cephem-4-carboxylate (syn isomer), mp 128° to 149° C. (dec.).

(2) 2,2,2-Trichloroethyl 2-methyl-7-[2-hydroxyimino-2-(2-aminothiazol-4-yl)acetamido]-3-cephem-4-carboxylate (syn isomer), which can be represented as 2,2,2-trichloroethyl 2-methyl-7-[2-hydroxyimino-2-(2-imino-2,3-dihydrothiazol-4-yl)acetamido]-3-cephem-4-carboxylate (syn isomer), mp 175° to 178° C. (dec.).

EXAMPLE 6

To a suspension of 2-methyl-7-[2-(2-formylaminothiazol-4-yl)glyoxylamino]-3-cephem-4-carboxylic acid, which can be represented as 2-methyl-7-[2-(2-formylimino-2,3-dihydrothiazol-4-yl)glyoxylamido]-3-cephem-4-carboxylic acid, (792 mg.) in water (20 ml.) was added sodium bicarbonate (168 mg.) with stirring. To thus obtained solution were added sodium acetate trihydrate (272.2 mg.) and 0-methylhydroxylamine hydrochloride (334 5mg.), and the mixture was stirred for 2 hours at 48° to 50° C. After cooling the reaction mixture, a saturated aqueous sodium bicarbonate solution (10 ml.) and ethyl acetate (15 ml.) were added thereto in order to dissolve the precipitated insoluble material. The aqueous layer was separated, washed with ethyl acetate, adjusted to pH 1 with 2 N hydrochloric acid and then extracted with ethyl acetate. The ethyl acetate extract was washed with a saturated aqueous sodium chloride solution, dried over magnesium sulfate and then concentrated. The residue was pulverized in diethyl ether, collected by filtration and then dried to give 2-methyl-7-[2-methoxyimino-2-(2-formylaminothiazol-4-yl)acetamido]-3-cephem-4-carboxylic acid (syn isomer), which can be represented as 2-methyl-7-[2-methoxyimino-2-(2-formylimino-2,3-dihydrothiazol-4-yl)acetamido]-3-cephem-4-carboxylic acid (syn isomer), (505 mg.). This compound was recrystallized from methanol to give white crystals of the pure object compound.

I.R. Spectrum (Nujol)
3270, 3200, 1775, 1650, 1530, 1280 cm$^{-1}$
N.M.R. Spectrum (d$_6$-dimethylsulfoxide, δ)
1.44 (3H, d, J=7Hz)
3.50-4.00 (1H, m)
3.90 (3H, s)
5.12 (1H, d, J=5Hz)
5.92 (1h, d, J=5Hz)
6.57 (1H, d, J=6Hz)
7.41 (1H, s)
8.51 (1H, s)

Similarly, the following compounds were obtained.
(1) 2-Methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), dp>241° C.
(2) 2,2,2-Trichloroethyl 2-methyl-7-[2-methoxyimino-2-(2-aminothiazol-4-yl)acetamido]-3-cephem-4-carboxylate (syn isomer), which can be represented as 2,2,2-trichloroethyl 2-methyl-7-[2-methoxyimino-2-(2-imino-2,3-dihydrothiazol-4-yl)acetamido]-3-cephem-4-carboxylate (syn isomer), mp 128° to 149° C. (dec.).

EXAMPLE 7

To a solution of 2,2,2-trichloroethyl 2-methyl-7-(2-hydroxyimino-3-oxo-4-bromobutyramido)-3-cephem-4-carboxylate (a mixture of syn and anti isomers) (0.51 g.) in ethanol (10 ml.) was added thiourea (0.068 g.), and the mixture was stirred for 1 hour at room temperature. The reaction mixture was concentrated under reduced pressure. To the residue were added ethyl acetate and water with stirring, and the ethyl acetate layer was separated. The remaining aqueous layer was adjusted to pH 7 and extracted with ethyl acetate. The ethyl acetate layer and extract were combined together, washed with water, dried over magnesium sulfate and then concentrated. The residue was pulverized in diethyl ether, collected by filtration and then dried to give pale brown powder of 2,2,2-trichloroethyl 2-methyl-7-[2-hydroxyimino-2-(2-aminothiazol-4-yl)acetamido]-3-cephem-4-carboxylate (syn isomer), which can be represented as 2,2,2-trichloroethyl 2-methyl-7-[2-hydroxyimino-2-(2-imino-2,3-dihydrothiazol-4-yl)acetamido]-3-cephem-4-carboxylate (syn isomer), mp 175° to 178° C. (dec.).

I.R. Spectrum (Nujol)
3300, 1785, 1740, 1710-1670, 1540, 1280, 1215, 1045, 715 cm$^{-1}$
N.M.R. Spectrum (d$_6$-dimethylsulfoxide, δ)
1.45 (3H, d, J=7Hz)
3.94 (1H, m)
5.06 (2H, s)
5.20 (1H, d, J=5Hz)
5.94 (1H, dd, J=5 and 9Hz)
6.64 (1H, s)
7.08 (2H, broad s)
9.47 (1H, d, J=9Hz)
11.28 (1H, s)

Similarly, the following compound was obtained.
p-Nitrobenzyl 2-methyl-7-[2-hydroxyimino-2-(2-aminothiazol-4-yl)acetamido]-3-cephem-4-carboxylate (syn isomer), which can be represented as p-nitrobenzyl 2-methyl-7-[2-hydroxyimino-2-(2-imino-2,3-dihydrothiazol-4-yl)acetamido]-3-cephem-4-carboxylate (syn isomer), powder.

I.R. Spectrum (Nujol)
3400, 3280, 3200, 1770, 1710, 1700, 1650, 1620 cm$^{-1}$
N.M.R. Spectrum (d$_6$-dimethylsulfoxide, δ)
ppm 1.44 (3H, d, J=7 Hz)
3.6-4.2 (1H, m)
5.25 (1H, d, J=4.5 Hz)
5.43 (2H, s)
5.97 (1H, dd, J=4.5 and 9 Hz)
6.73 (1H, s)
6.76 (1H, d, J=7 Hz)
7.74 (2H, d, J=9 Hz)
8.29 (2H, d, J=9 Hz)
9.59 (1H, d, J=9 Hz)

EXAMPLE 8

To a mixture of 2,2,2-trichloroethyl 2-methyl-7-(2-methoxyimino-3-oxo-4-bromobutyramido)-3-cephem-4-carboxylate (a mixture of syn and anti isomers) (0.94 g.) and ethanol (10 ml.) was added thiourea (0.12 g.), and the mixture was stirred for 40 minutes at room temperature. The reaction mixture was concentrated under reduced pressure, and the residue was shaken with ethyl acetate and water. The ethyl acetate layer was separated, and the remaining aqueous layer was neutralized with sodium bicarbonate and then extracted with ethyl acetate. Thus obtained ethyl acetate layers were combined together, washed with water, dried over magnesium sulfate, treated with activated charcoal and then concentrated under reduced pressure. The residue was pulverized in diethyl ether, collected by filtration and then dried to give 2,2,2-trichloroethyl 2-methyl-7-[2-methoxyimino-2-(2-aminothiazol-4-yl)acetamido]-3-cephem-4-carboxylate (syn isomer), which can be represented as 2,2,2-trichloroethyl 2-methyl-7-[2-methoxyimino-2-(2-imino-2,3-dihydrothiazol-4-yl)acetamido]-3-cephem-4-carboxylate (syn isomer), (0.6 g.). This compound was subjected to column chromatography on silica gel using a mixed solvent of benzene, ethyl acetate and acetic acid (10:10:1) as a developer, and the eluates containing the object compound were collected, washed with water, dried over magnesium sulfate and then concentrated under reduced pressure. The residue was pulverized in diethyl ether, collected by filtration and then dried to give pale brown powder of the purified object compound (syn isomer) (0.16 g.), mp 128° to 149° C. (dec.).

I.R. Spectrum (Nujol)
3100-3500, 1785, 1735, 1675, 1620, 1530, 1280, 1218, 710 cm$^{-1}$
N.M.R. Spectrum (d$_6$-dimethylsulfoxide, δ)
1.45 (3H, d, J=7 Hz)
3.82 (3H, s)
3.92 (1H, m)
5.05 (2H, s)

5.20 (1H, d, J=5 Hz)
5.97 (1H, dd, J=5 and 9 Hz)
6.73 (1H, s)
6.77 (1H, d, J=6 Hz)
7.10 (2H, broad s)
9.65 (1H, d, J=9 Hz)

Similarly, the following compounds were obtained.

(1) 2-Methyl-7-[2-methoxyimino-2-(2- formylaminothiazol-4-yl)acetamido]-3-cephem-4-carboxylic acid (syn isomer), which can be represented as 2-methyl-7-[2-methoxyimino-2-(2-formylimino-2,3-dihydrothiazol-4-yl)acetamido]-3-cephem-4-carboxylic acid (syn isomer), mp 174° to 204° C. (dec.).

(2) 2-Methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), dp>241° C.

(3) Pivaloyloxymethyl 2-methyl-7-[2-methoxyimino-2-(2-aminothiazol-4-yl)acetamido]-3-cephem-4-carboxylate (syn isomer), which can be represented as pivaloyloxymethyl 2-methyl-7-[2-methoxyimino-2-(2-imino-2,3-dihydrothiazol-4-yl)acetamido]-3-cephem-4-carboxylate (syn isomer), mp 165° to 170° C. (dec.).

EXAMPLE 9

To a solution of 2,2,2-trichloroethyl 2-methyl-7-[2-hydroxyimino-2-(2-aminothiazol-4-yl)acetamido]3-cephem-4-carboxylate (syn isomer), which can be represented as 2,2,2-trichloroethyl 2-methyl-7-[2-hydroxyimino-2-(2-imino-2,3-dihydrothiazol-4-yl)acetamido]-3-cephem-4-carboxylate (syn isomer), (125 mg.) in dioxane (5 ml.) was added dropwise 0.1 M solution of diazomethane in diethyl ether till the starting compound disappeared. After the reaction mixture was concentrated, the residue was pulverized in diethyl ether, collected by filtration and then dried to give brown powder of 2,2,2-trichloroethyl 2-methyl-7-[2-methoxyimino-2-(2-aminothiazol-4-yl)acetamido]-3-cephem-4-carboxylate (syn isomer), which can be represented as 2,2,2-trichloroethyl 2-methyl-7-[2-methoxyimino-2-(2-imino-2,3-dihydrothiazol-4-yl)acetamido]-3-cephem-4-carboxylate (syn isomer), (110 mg.), mp 128° to 149° C. (dec.).

Similarly, the following compound was obtained.

(1) Pivaloyloxymethyl 2-methyl-7-[2-methoxyimino-2-(2-aminothiazol-4-yl)acetamido]-3-cephem-4-carboxylate (syn isomer), which can be represented as pivaloyloxymethyl 2-methyl-7-[2-methoxyimino-2-(2-imino-2,3-dihydrothiazol-4-yl)acetamido]-3-cephem-4-carboxylate (syn isomer), mp 165° to 170° C. (dec.).

EXAMPLE 10

To a solution of 2,2,2-trichloroethyl 2-methyl-7-[2-methoxyimino-2-(2-aminothiazol-4-yl)acetamido]-3-cephem-4-carboxylate (syn isomer), which can be represented as 2,2,2-trichloroethyl 2-methyl-7-[2-methoxyimino-2-(2-imino-2,3-dihydrothiazol-4-yl)acetamido]-3-cephem-4-carboxylate (syn isomer), (0.1 g.) in tetrahydrofuran (2 ml.) and glacial acetic acid (0.25 ml.) was added zinc powder (0.1 g.) all at once with stirring at keeping the temperature below 25° C. in an ice-bath and then the mixture was stirred for 1 hour at room temperatures. To the reaction mixture was further added zinc powder (0.1 g.) and the mixture was stirred for 1 hour at the same temperature. The reaction mixture was filtered, and the insoluble material was washed with a small amount of tetrahydrofuran. After the filtrate and the washing were combined together, the solvents were distilled off. To the residue were added 5% aqueous sodium bicarbonate solution and ethyl acetate so that the aqueous layer became pH 7 to 8, and the mixture was filtered, and then the aqueous layer was separated. The aqueous layer was adjusted to pH 2 to 3 with 2 N hydrochloric acid and then concentrated slightly. Thus obtained aqueous layer was subjected to column chromatography (non-ionic adsorption resin, Diaion HP 20 prepared by Mitsubishi Chemical Industries) and the column was washed with water and then eluted with 20% methanol and 40% methanol in turn. The eluates containing the object compound were collected and then lyophilized to give white powder of 2-methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), (0.015 g.), mp 230° to 235° C. (dec.).

Similarly, the following compounds were obtained.

(1) 2-Methyl-7-[2-methoxyimino-2-(2-formylaminothiazol-4-yl)acetamido]-3-cephem-4-carboxylic acid (syn isomer), which can be represented as 2-methyl-7-[2-methoxyimino-2-(2-formylimino-2,3-dihydrothiazol-4-yl)acetamido]-3-cephem-4-carboxylic acid (syn isomer), mp 174° to 204° C. (dec.).

(2) 2-Methyl-7-[2-hydroxyimino-2-(2-aminothiazol-4-yl)acetamido]-3-cephem-4-carboxylic acid (syn isomer), which can be represented as 2-methyl-7-[2-hydroxyimino-2-(2-imino-2,3-dihydrothiazol-4-yl)acetamido]-3-cephem-4-carboxylic acid (syn isomer).

I.R. Spectrum (Nujol)
3250, 1765, 1625 cm$^{-1}$
N.M.R. Spectrum (d$_6$-dimethylsulfoxide, δ)
ppm 1.42 (3H, d, J=6.8 Hz)
3.54–3.94 (1H, m)
5.23 (1H, d, J=6 Hz)
5.82 (1H, dd, J=6 and 8 Hz)
6.40 (1H, d, J=6.8 Hz)
6.64 (1H, s)
9.44 (1H, d, J=8 Hz)

EXAMPLE 11

To a suspension of 2-methyl-7-[2-methoxyimino-2-(2-aminothiazol-4-yl)acetamido]-3-cephem-4-carboxylic acid (syn isomer), which can be represented as 2-methyl-7-[2-methoxyimino-2-(2-imino-2,3-dihydrothiazol-4-yl)acetamido]-3-cephem-4-carboxylic acid (syn isomer), (4.8 g.) in water (48 ml.) was added dropwise 1 N aqueous sodium hydroxide solution at the rate that the pH value of the mixture was not more than 7. The mixture was filtered and then lyophilized to give sodium 2-methyl-7-[2-methoxyimino-2-(2-aminothiazol-4-yl)acetamido]-3-cephem-4-carboxylate (syn isomer), which can be represented as sodium 2-methyl-7-[2-methoxyimino-2-(2-imino-2,3-dihydrothiazol-4-yl)acetamido]-3-cephem-4-carboxylate (syn isomer), (4.8 g.), mp>250° C. This compound is suspended in dried dimethylformamide (20 ml.), and to the suspension was added iodomethyl pivalate (2.30 g.) with vigorous stirring under cooling to 3° to 5° C., and then the mixture was stirred for 20 minutes at the same temperature. The reaction mixture was poured into a mixture of ethyl acetate (60 ml.) and ice-water (10 ml.), and the mixture was well shaken. The ethyl acetate layer was separated, washed with a saturated aqueous sodium bicarbonate solution, water and a saturated aqueous sodium chloride solution in turn. After the ethyl acetate layer was dried over magnesium sulfate, ethyl acetate was distilled off under reduced pressure. The residual oil was pulverized in diethyl ether (25 ml.), collected by filtration and then dried to give pivaloyloxymethyl 2-methyl-7-[2-methoxyimino-2-(2-aminothiazol-4-yl)acetamido]-3-cephem-4-carboxylate (syn isomer), which can be represented as pivaloyloxymethyl 2-methyl-7-[2-methoxyimino-2-(2-imino-2,3-dihydrothiazol-4-yl)acetamido]-3-cephem-4-carboxylate (syn isomer), (1.44 g.), mp 165° to 170° C. (dec.).

I.R. Spectrum (Nujol)
3340, 1787, 1757, 1678, 1637, 1634, 1283, 1218, 1158, 1132, 1098, 1034, 996 cm$^{-1}$ N.M.R. Spectrum (d$_6$-dimethylsulfoxide, δ)
1.18 (3H, s)
1.47 (3H, d, J=7 Hz)
3.6–4.1 (3H, s)
5.18 (1H, d, J=6 Hz)
5.78–5.96 (3H, m)
6.70 (1H, d, J=6 Hz)
6.76–6.88 (1H, s)
9.65 (1H, broad d, J=8 Hz)

EXAMPLE 12

To dimethylformamide (0.65 g) was added dried ethyl acetate (3 ml), and the mixture was solidified by dropwise addition of phosphorus oxychloride (1.37 g) under cooling at 0° C. in dry ice-acetone bath over 15 minutes followed by stirring at the same temperature for a while. Dried ethyl acetate (20 ml) was added thereto and 2-ethoxyimino-2-(2-formylaminothiazol-4-yl)acetic acid (syn isomer), which can be represented as 2-ethoxyimino-2-(2-formylimino-2,3-dihydrothiazol-4-yl)acetic acid (syn isomer), (2.00 g) was added thereto. The resulting mixture was stirred for an hour at the same temperature and thereto was added ethyl acetate (30 ml) and stirring was continued at the same temperature for an hour, during which period a homogeneous solution was obtained. Thus obtained solution was added dropwise over 15 minutes at −15° C. to a solution, which was prepared by stirring a mixture of 2-methyl-7-amino-3-cephem-4-carboxylic acid (1.60 g) and trimethylsilylacetamide (6.86 g) in ethyl acetate (100 ml) for an hour at room temperature. The mixture was stirred for an hour at the same temperature and thereto was added water (30 ml) and then the temperature of the mixture was permitted to rise to room temperature. The precipitates were collected by filtration washed with water and then dried over phosphorus pentoxide under reduced pressure to give 2-methyl-7-[2-ethoxyimino-2-(2-formylaminothiazol-4-yl)acetamido]-3-cephem-4-carboxylic acid (syn isomer), which can be represented as 2-methyl-7-[2-ethoxyimino-2-(2-formylimino-2,3-dihydrothiazol-4-yl)acetamido]-3-cephem-4-carboxylic acid (syn isomer), (1.68 g). The ethyl acetate layer in the mother liquor was separated, washed with water, dried over magnesium sulfate and then concentrated under reduced pressure to give powder of the same compound (1.54 g). Total yield: 3.22 g.

I.R. Spectrum (Nujol)
3350, 3240, 3190, 1775, 1700, 1650, 1620 cm$^{-1}$

N.M.R. Spectrum (d$_6$-dimethylsulfoxide, δ)
1.28 (3H, t, J=7 Hz)
1.47 (3H, d, J=8 Hz)
3.68–4.2 (1H, m)
4.18 (2H, q, J=7 Hz)
5.15 (1H, d, J=5 Hz)
5.94 (1H, d, d, J=5 and 8 Hz)
6.58 (1H, d, J=6 Hz)
7.40 (1H, s)
8.52 (1H, s)
9.65 (1H, d, J=8 Hz)
11.64 (1H, broads)

EXAMPLE 13

A solution of 2-methyl-7-[2-ethoxyimino-2-(2-formylaminothiazol-4-yl)acetamido]-3-cephem-4-carboxylic acid (syn isomer), which can be represented as 2-methyl-7-[2-ethoxyimino-2-(2-formylimino-2,3-dihydrothiazol-4-yl)acetamido]-3-cephem-4-carboxylic acid (syn isomer), (3.0 g) in methanol (40 ml) was cooled in an ice-water bath and thereto was added dropwise a solution of concentrated hydrochloric acid (3.8 g) in methanol (12 ml) with stirring and then stirring was continued at room temperature. After 35 minutes stirring a homogeneous solution was formed and then 2 hours later precipitates appeared and thereafter diethyl ether (300 ml) was added thereto. The precipitates were collected by filtration, washed with diethyl ether and then dried over phosphorus pentoxide under reduced pressure to give powder of 2-methyl-7-[2-ethoxyimino-2-(2-aminothiazol-4-yl)acetamido]-3-cephem-4-carboxylic acid hydrochloride (syn isomer), which can be represented as 2-methyl-7-[2-ethoxyimino-2-(2-imino-2,3-dihydrothiazol-4-yl)acetamido]-3-cephem-4-carboxylic acid hydrochloride (syn isomer), (2.6 g).

I.R. Spectrum (Nujol)
3350, 1790, 1730, 1670, 1630 cm$^{-1}$

N.M.R. Spectrum (d$_6$-dimethylsulfoxide, δ)
1.30 (3H, t, J=6 Hz)
1.47 (3H, d, J=6 Hz)
3.6–4.5 (1H, m)
4.25 (2H, q, J=6 Hz)
5.17 (1H, d, J=5 Hz)
5.92 (1H, d, d, J=5 and 8 Hz)
6.60 (1H, d, J=6 Hz)
6.97 (1H, s)
9.82 (1H, d, J=8 Hz)

EXAMPLE 14

The Vilsmeier reagent was prepared from dimethylformamide (0.44 g) and phosphorus oxychloride (0.92 g) in the conventional manner, and thereto was added ethyl acetate (20 ml). To the mixture was added 2-isopropoxyimino-2-(2-formylaminothiazol-4-yl)acetic acid (syn isomer), which can be represented as 2-isopropoxyimino-2-(2-formylimino-2,3-dihydrothiazol-4-yl)acetic acid (syn isomer), (1.29 g) under cooling at −5° to 0° C. with stirring and then stirring was continued for 20 minutes to give a clear solution. Thus obtained solution was added at a time to solution, which was prepared by warming a mixture of 2-methyl-7-amino-3-cephem-4-carboxylic acid (1.44 g) and trimethylsilylacetamide (4.6 g) in ethyl acetate (30 ml) at 40° C. followed by stirring for 30 minutes, under cooling at −20° to −15° C. with stirring. The resulting mixture was stirred for 1.5 hours at the same temperature and thereto was added water (20 ml). The mixture was stirred for 20 minutes at room temperature. The precipitates were collected by filtration, washed with a small amount of ethyl acetate, washed well with water and then dried to give 2-methyl-7-[2-isopropoxyimino-2-(2-formylaminothiazol-4-yl)acetamido]-3-cephem-4-carboxylic acid (syn isomer), which can be represented as 2-methyl-7-[2-isopropoxyimino-2-(2-formylimino-2,3-dihydrothiazol-4-yl)acetamido]-3-cephem-4-carboxylic acid (syn isomer), (1.8 g).

I.R. Spectrum (Nujol)
3480, 3300, 3180, 1780, 1740, 1700, 1660 cm$^{-1}$
N.M.R. Spectrum (d$_6$-dimethylsulfoxide, δ)
1.14 (6H, d, J=7 Hz)
1.4 (3H, d, J=6 Hz)
3.8 (1H, m)
4.35 (1H, m)
5.1 (1H, d, J=5 Hz)
5.87 (1H, d, d, J=5 and 8 Hz)
6.5 (1H, d, J=6 Hz)
7.35 (1H, s)
8.45 (1H, s)
9.55 (1H, d, J=8 Hz)

EXAMPLE 15

To a mixture of methanol (13 ml) and tetrahydrofuran (13 ml) was dissolved 2-methyl-7-[2-isopropoxyimino-2-(2-formylaminothiazol-4-yl)acetamido]-3-cephem-4-carboxylic acid (syn isomer), which can be represented as 2-methyl-7-[2-isopropoxyimino-2-(2-formylimino-2,3-dihydrothiazol-4-yl)acetamido]-3-cephem-4-carboxylic acid (syn isomer), (1.7 g) and thereto was added concentrated hydrochloric acid (1.5 ml) with stirring at room temperature and then stirring was continued for 2 hours at room temperature. The reaction mixture was concentrated to dryness and the solid was dissolved in water (100 ml) by adding sodium bicarbonate, whereby the resulting mixture was adjusted to pH 7.0. The solution was adjusted to pH 3.0 with concentrated hydrochloric acid under ice-cooling. Precipitates were collected by filtration, washed with water and then dried to give 2-methyl-7-[2-isopropoxyimino-2-(2-aminothiazol-4-yl)acetamido]-3-cephem-4-carboxylic acid (syn isomer), which can be represented as 2-methyl-7-[2-isopropoxyimino-2-(2-imino-2,3-dihydrothiazol-4-yl)acetamido]-3-cephem-4-carboxylic acid (syn isomer), (1.2 g).

I.R. Spectrum (Nujol)
3350, 1780, 1670, 1600 cm$^{-1}$
N.M.R. Spectrum (d$_6$-dimethylsulfoxide, δ)
1.20 (6H, d, J=6 Hz)
1.43 (1H, d, J=6 Hz)
3.83 (1H, m)
4.27 (1H, m)
5.12 (1H, d, J=5 Hz)
5.87 (1H, d, d, J=5 and 9 Hz)
6.55 (1H, d, J=6 Hz)
6.72 (1H, s)
7.23 (2H, broads)
9.49 (1H, d, J=9 Hz)

Similarly, the following compounds were obtained.

(1) 2-Methyl-7-[2-propoxyimino-2-(2-aminothiazol-4-yl)acetamido]-3-cephem-4-carboxylic acid (syn isomer), which can be represented as 2-methyl-7-[2-propoxyimino-2-(2-imino-2,3-dihydrothiazol-4-yl)acetamido]-3-cephem-4-carboxylic acid (syn isomer).

(2) 2-Methyl-7-[2-butoxyimino-2-(2-amino-thiazol-4-yl)acetamido]-3-cephem-4-carboxylic acid (syn isomer), which can be represented as 2-methyl-7-[2-butoxyimino-2-(2-imino-2,3-dihydrothiazol-4-yl)acetamido]-3-cephem-4-carboxylic acid (syn isomer).

(3) 2-Methyl-7-[2-isobutoxyimino-2-(2-aminothiazol-4-yl)acetamido]-3-cephem-4-carboxylic acid (syn isomer), which can be represented as 2-methyl-7-[2-isobutoxyimino-2-(2-imino-2,3-dihydrothiazol-4-yl)acetamido]-3-cephem-4-carboxylic acid (syn isomer).

EXAMPLE 16

To a solution of N,N-dimethylformamide (1.23 g) and ethyl acetate (9 ml) was added dropwise phosphorus oxychloride (2.58 g) at −10° to −5° C. with stirring, and the mixture was stirred for 30 minute at the same temperature. To the mixture were added 2-hexyloxyimino-2-(2-formylaminothiazol-4-yl)acetic acid (syn isomer), which can be represented as 2-hexyloxyimino-2-(2-formylimino-2,3-dihydrothiazol-4-yl)acetic acid (syn isomer), (4.2 g) and ethyl acetate (33 ml), and the mixture was stirred for 30 minutes at −10° to −5° C. and then cooled to −20° C. Thus obtained solution was added to a solution, which was prepared by stirring a mixture of 2-methyl-7-amino-3-cephem-4-carboxylic acid (3 g) and trimethylsilylacetamide (11 g) in ethyl acetate (33 ml), with stirring under cooling to −10° C. The mixture was stirred for 30 minutes at −10° C. and thereto was added water 50 ml. The mixture was extracted twice with ethyl acetate. The combined extracts were washed with an aqueous solution of sodium chloride and the precipitates were collected by filtration and then dried to give 2-methyl-7-[2-hexyloxyimino-2-(2-formylaminothiazol-4-yl)acetamido]-3-cephem-4-carboxylic acid (syn isomer), which can be represented as 2-methyl-7-[2-hexyloxyimino-2-(2-formylimino-2,3-dihydrothiazol-4-yl)acetamido]-3-cephem-4-carboxylic acid (syn isomer), (4.3 g). The filtrate was evaporated to give further the same object compound (1.15 g).

I.R. Spectrum (Nujol) 3270, 3180, 1790, 1700, 1655 cm$^{-1}$
N.M.R. Spectrum (d$_6$-dimethylsulfoxide, δ) 0.6–2.1 (14H, m), 3.6–4.4 (3H, m), 5.15 (1H, d, J=5), 5.93 (1H, d, d, J=5, 8 Hz), 6.57 (1H, d, J=6), 7.40 (1H, s) 8.54 (1H, s), 9.62 (1H, d, J=8 Hz), 12.7 (1H, s)

Similarly, the following compounds were obtained.

(1) 2-Methyl-7-[2-propoxyimino-2-(2-formylaminothiazol-4-yl)acetamido]-3-cephem-4-carboxylic acid (syn isomer), which can be represented as 2-methyl-7-[2-propoxyimino-2-(2-formylimino-2,3-dihydrothiazol-4-yl)acetamido]-3-cephem-4-carboxylic acid (syn isomer).

I.R. Spectrum (Nujol) 3450, 3300, 3050, 1780, 1730, 1690, 1660 cm$^{-1}$
N.M.R. Spectrum (d$_6$-dimethylsulfoxide, δ) 0.96 (3H, t, J=6 Hz), 1.48 (3H, d, J=6 Hz), 1.68 (2H, m), 3.85 (1H, m), 4.02 (2H, t, J=6 Hz), 5.14 (1H, d, J=5 Hz), 5.96 (1H, d, d, J=5, 9 Hz), 6.6 (1H, d, J=6 Hz), 7.42 (1H, s), 8.56 (1H, s), 9.70 (1H, d, J=9 Hz)

(2) 2-Methyl-7-[2-propoxyimino-2-(2-aminothiazol-4-yl)acetamido]-3-cephem-4-carboxylic acid (syn isomer), which can be represented as 2-methyl-7-[2-propoxyimino-2-(2-imino-2,3-dihydrothiazol-4-yl)acetamido]-3-cephem-4-carboxylic acid (syn isomer).

I.R. Spectrum (Nujol) 3330, 3080, 1780, 1670 cm$^{-1}$ (3) 2-Methyl-7-[2-hexyloxyimino-2-(2-aminothiazol-4-yl)acetamido]-3-cephem-4-carboxylic acid (syn isomer), which can be represented as 2-methyl-7-[2-hexyloxyimino-2-(2-imino-2,3-dihydrothiazol-4-yl)acetamido]-3-cephem-4-carboxylic acid (syn isomer).

I.R. Spectrum (Nujol) 3300, 3200, 1780, 1670, 1630 cm$^{-1}$ (4) Hexanoyloxymethyl 2-methyl-7-[2-hexyloxyimino-2-(2-aminothiazol-4-yl)acetamido]-3-cephem-4-carboxylate (syn isomer), which can be represented as hexanoyloxymethyl 2-methyl-7-[2-hexyloxyimino-2-(2-imino-2,3-dihydrothiazol-4-yl)acetamido]-3-cephem-4-carboxylate (syn isomer).

I.R. Spectrum (Nujol) 3340, 3200 (broad), 3150 (broad), 1790 (broad), 1750–1790, 1680, 1630 cm$^{-1}$

EXAMPLE 17

A solution of 2-methyl-7-[2-hexyloxyimino-2-(2-formylaminothiazol-4-yl)acetamido]-3-cephem-4-carboxylic acid (syn isomer), which can be represented as 2-methyl-7-[2-hexyloxyimino-2-(2-formylimino-2,3-dihydrothiazol-4-yl)acetamido]-3-cephem-4-carboxylic acid (syn isomer), (5.3 g) and concentrated hydrochloric acid (4.2 g) in a mixture of methanol (53 ml) and tetrahydrofuran (40 ml) was stirred for 2 hours at 30° C., and then evaporated to dryness. The residue was dissolved in an aqueous solution of sodium bicarbonate (500 ml) and then filtered. The filtrate was adjusted to pH 3.5 with 10% hydrochloric acid with stirring under ice-cooling and further stirred for 30 minutes at the same temperature. The precipitates were collected by filtration, washed with water and then dried to give 2-methyl-7-[2-hexyloxyimino-2-(2-aminothiazol-4-yl)acetamido]-3-cephem-4-carboxylic acid (syn isomer), which can be represented as 2-methyl-7-[2-hexyloxyimino-2-(2-imino-2,3-dihydrothiazol-4-yl)acetamido]-3-cephem-4-carboxylic acid (syn isomer), (4.45 g).

I.R. Spectrum (Nujol) 3330, 3200, 1780, 1670, 1630 cm$^{-1}$

N.M.R. Spectrum (d$_6$-dimethylsulfoxide, δ) 0.6–2.0 (11H, m), 3.5–4.3 (3H, m), 5.09 (1H, d, J=5), 5.87 (1H, d, d, J=5, 8 Hz), 6.56 (1H, d, J=6), 6.70 (1H, s), 7.22 (2H, s), 9.53 (1H, d, J=8)

Similarly, the following compound was obtained.

(1) 2-Methyl-7-propoxyimino-2-(2-aminothiazol-4-yl)acetamido-3-cephem-4-carboxylic acid (syn isomer), which can be represented as 2-methyl-7-[2-propoxyimino-2-(2-imino-2,3-dihydrothiazol-4-yl)acetamido-3-cephem-4-carboxylic acid (syn isomer).

I.R. Spectrum (Nujol) 3330, 3080, 1780, 1670 cm$^{-1}$

N.M.R. Spectrum (d$_6$-dimethylsulfoxide, δ) 0.87 (3H, t, J=7 Hz), 1.40 (3H, d, J=6 Hz), 1.57 (2H, m), 3.80 (1H, m), 4.0 (2H, t, J=7 Hz), 5.08 (1H, d, J=5 Hz), 5.83 (1H, d, d, J=5, 9 Hz), 6.72 (1H, d, J=6 Hz), 6.83 (1H, s), 7.22 (1H, m), 9.65 (1H, d, J=9 Hz)

EXAMPLE 18

To a suspension of 2-methyl-7-[2-hexyloxyimino-2-(2-aminothiazol-4-yl)acetamido]-3-cephem-4-carboxylic acid (syn isomer), which can be represented as 2-methyl-7-[2-hexyloxyimino-2-(2-imino-2,3-dihydrothiazol-4-yl)acetamido]-3-cephem-4-carboxylic acid (syn isomer), (1.21 g) in water (150 ml) was added sodium bicarbonate (217 mg) with stirring, and the resulting solution was lyophilized. The residue was dried over phosphorus pentoxide and dissolved in N,N-dimethylformamide (10 ml) and then stirred at 2° to 3° C. To the solution was added iodomethyl hexanoate (0.66 g) and the mixture was stirred for 10 minutes. The mixture was poured into ice-water and then extracted twice with ethyl acetate. The combined extracts were washed three times with an aqueous solution of sodium chloride, dried over magnesium sulfate and then evaporated. The resulting oil was pulverized in n-hexane, collected by filtration and then dried to give powder of hexanoyloxymethyl 2-methyl-7-[2-hexyloxyimino-2-(2-aminothiazol-4-yl)acetamido]-3-cephem-4-carboxylate (syn isomer), which can be represented as hexanoyloxymethyl 2-methyl-7-[2-hexyloxyimino-2-(2-imino-2,3-dihydrothiazol-4-yl)acetamido]-3-cephem-4-carboxylate (syn isomer), (0.66 g).

I.R. Spectrum (Nujol) 3340, 3200 (broad), 3150 (broad), 1790 (broad), 1750–1790 (broad), 1680, 1630 cm$^{-1}$ N.M.R. Spectrum (d$_6$-dimethylsulfoxide, δ) 0.5–2.1 (23H, m), 2.40 (2H, t, J=6 Hz), 3.6–4.4 (3H, m), 5.18 (1H, d, J=5), 5.6–6.2 (3H, m), 6.6–7.0 (2H, m), 7.32 (2H, broad s), 9.60 (1H, d, J=9 Hz)

What is claimed is:

1. A compound of the formula:

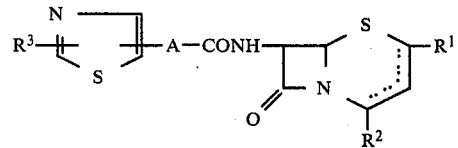

wherein
R$^1$ is (C$_1$ to C$_6$)alkyl,
R$^2$ is carboxy or a protected carboxy group,
R$^3$ is amine or a protected amino group and
A is (C$_2$ to C$_6$)-alkoxyimino(C$_1$ to C$_6$)alkylene, and pharmaceutically acceptable salt thereof.

2. A pharmaceutical composition comprising a compound of claim 1 or pharmaceutically acceptable salt thereof in association with a pharmaceutically acceptable, substantially non-toxic carrier or excipient.

3. 2-methyl-7-[2-ethoxyimino-2-(2-formylimino-2,3-dihydrothiazol-4-yl)acetamido]-3-cephem-4-carboxylic acid (syn isomer).

4. 2-methyl-7-[2-ethoxyimino-2-(2-imino-2,3-dihydrothiazol-4-yl)acetamido]-3-cephem-4-carboxylic acid hydrochloride (syn isomer).

5. 2-methyl-7-[2-isopropoxyimino-2-(2-formylimino-2,3-dihydrothiazol-4-yl)acetamido]-3-cephem-4-carboxylic acid (syn isomer).

6. 2-methyl-7-[2-isopropoxyimino-2-(2-imino-2,3-dihydrothiazol-4-yl)acetamido]-3-cephem-4-carboxylic acid (syn isomer).

7. 2-methyl-7-[2-propoxyimino-2-(2-imino-2,3-dihydrothiazol-4-yl)acetamido]-3-cephem-4-carboxylic acid (syn isomer).

8. 2-methyl-7-[2-butoxyimino-2-(2-imino-2,3-dihydrothiazol-4-yl)acetamido-3-cephem-4-carboxylic acid (syn isomer).

9. 2-methyl-7-(2-isobutoxyimino-2-(2-imino-2,3-dihydrothiazol-4-yl)acetamido]-3-cephem-4-carboxylic acid (syn isomer).

10. 2-methyl-7-[2-hexyloxyimino-2-(2-formylimino-2,3-dihydrothiazol-4-yl)acetamido]-3-cephem-4-carboxylic acid (syn isomer).

11. 2-methyl-7-[2-propoxyimino-2-(2-formylimino-2,3-dihydrothiazol-4-yl)acetamido]-3-cephem-4-carboxylic acid (syn isomer).

12. 2-methyl-7-[2-hexyloxyimino-2-(2-imino-2,3-dihydrothiazol-4-yl)acetamido]-3-cephem-carboxylic acid (syn isomer).

13. Hexanoyloxymethyl 2-methyl-7-[2-hexyloxyimino-2-(2-imino-2,3-dihydrothiazol-4-yl)acetamido]-3-cephem-4-carboxylate (syn isomer).

14. 2-methyl-7-[2-hexyloxyimino-2-(2-formylimino-2,3-dihydrothiazol-4-yl)acetamido]-3-cephem-4-carboxylic acid (syn isomer).

* * * * *

UNITED STATES PATENT AND TRADEMARK OFFICE
CERTIFICATE OF CORRECTION

PATENT NO. : 4,299,829
DATED : November 10, 1981
INVENTOR(S) : TAKASHI KAMIYA ET AL It is certified that error appears in the above-identified patent and that said Letters Patent are hereby corrected as shown below:

In column 36, line 25, "amine" should read --amino--.

In column 36, line 60, "-3-cephem-carboxylic acid" should read-- -3-cephem-4-carboxylic acid--.

Signed and Sealed this

Thirtieth Day of March 1982

[SEAL]

Attest:

Attesting Officer

GERALD J. MOSSINGHOFF
Commissioner of Patents and Trademarks